US011612560B2

(12) United States Patent
Kahaleh et al.

(10) Patent No.: US 11,612,560 B2
(45) Date of Patent: Mar. 28, 2023

(54) TREATMENT OF RAYNAUD'S PHENOMENON BY INHIBITION OF TRANSIENT RECEPTOR POTENTIAL MELASTATIN-8 (TRPM-8)

(71) Applicant: The University of Toledo, Toledo, OH (US)

(72) Inventors: Bashar Kahaleh, Toledo, OH (US); Nezam Altorok, Toledo, OH (US); Sai H S. Boddu, Toledo, OH (US); Vivek Nagaraja, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 15/757,833

(22) PCT Filed: Sep. 7, 2016

(86) PCT No.: PCT/US2016/050500
§ 371 (c)(1),
(2) Date: Mar. 6, 2018

(87) PCT Pub. No.: WO2017/044458
PCT Pub. Date: Mar. 16, 2017

(65) Prior Publication Data
US 2018/0338907 A1   Nov. 29, 2018

Related U.S. Application Data

(60) Provisional application No. 62/215,529, filed on Sep. 8, 2015.

(51) Int. Cl.
| | | |
|---|---|---|
| *A61K 9/00* | (2006.01) | |
| *A61K 9/06* | (2006.01) | |
| *A61K 31/4174* | (2006.01) | |
| *A61K 47/10* | (2017.01) | |
| *A61K 31/55* | (2006.01) | |
| *A61K 47/14* | (2017.01) | |
| *A61K 47/24* | (2006.01) | |
| *A61P 17/00* | (2006.01) | |
| *A61K 47/38* | (2006.01) | |

(52) U.S. Cl.
CPC .............. *A61K 9/0014* (2013.01); *A61K 9/06* (2013.01); *A61K 31/4174* (2013.01); *A61K 31/55* (2013.01); *A61K 47/10* (2013.01); *A61K 47/14* (2013.01); *A61K 47/24* (2013.01); *A61K 47/38* (2013.01); *A61P 17/00* (2018.01)

(58) Field of Classification Search
CPC combination set(s) only.
See application file for complete search history.

(56) References Cited

U.S. PATENT DOCUMENTS

| | | | | |
|---|---|---|---|---|
| 4,855,294 A | * | 8/1989 | Patel ...................... | A61K 47/14 514/212.03 |
| 5,895,642 A | * | 4/1999 | Sanders ................ | A61K 8/046 424/59 |
| 6,391,879 B1 | * | 5/2002 | Reeves ................. | A61K 47/10 514/254.07 |
| 2008/0095720 A1 | | 4/2008 | Meldrum | |

FOREIGN PATENT DOCUMENTS

| | | | |
|---|---|---|---|
| CN | 102423293 B | | 5/2013 |
| EP | 0/484/529 | * | 4/1997 |
| WO | WO 2004/012725 | * | 2/2004 |
| WO | WO 2005/063224 | * | 7/2005 |
| WO | 2012120398 A1 | | 9/2012 |
| WO | 2017044458 A1 | | 3/2017 |

OTHER PUBLICATIONS

Dermatologist (Focus on Propylene Glycol, Issue vol. 21—Issue 8—Aug. 2013).*
Ghosal (Hydroxypropyl methblcellulose in drug delivery, Der Pharmacia Sinica, 2011, 2 (2): 152-168).*
Lachenmeier (Safety evaluation of topical applications of ethanol on the skin and inside the oral cavity, Journal of Occupational Medicine and Toxicology 2008, 3:26).*
Fernandez et al., "Pathogenic Role of Store-Operated and Receptor-Operated Ca$^{2+}$ Channels in Pulmonary Arterial Hypertension", Journal of Signal Transduction, 2012, pp. 1-16.
Goundry et al., "Diagnosis and management of Raynaud's phenomenon", British Medical Journal, 2012, vol. 344, pp. 37-42.
Hashem et al., "Formulation, Characterization, and Clinical Evaluation of Microemulsion Containing Clotrimazole for Topical Delivery", American Association of Pharmaceutical Scientists PharmSciTech, 2011, vol. 12, No. 3, pp. 879-886.
Malkia et al., "Differential role of the menthol-binding residue Y745 in the antagonism of thermally gated TRPM8 channels", Molecular Pain, 2009, vol. 5, No. 62, pp. 1-13.
Shah, et al., "Skin permeating nanogel for the cutaneous co-delivery of two anti-inflammatory drugs", Biomaterials, 2012, vol. 33, No. 5, pp. 1607-1617.
Wang et al., "Enhanced Expression of the Cold-Sensing Receptor-TRPM8 in Scleroderma Endothelial Cells and Skin and Endothelial Dysfunction Following TRPM8 Activation", American College of Rheumatology, 2013, Annual Meeting, Abstract 668. Retrieved on May 15, 2019 from the Internet; URL: https://acrabstracts.org/abstract/enhanced-expression-of-the-cold-sensing-receptor-trpm8-in-scleroderma-endothelial-cells-and-skin-and-endothelial-dysfunction-following-trpm8-activation/.
Kahaleh et al., "The Presence of a Cold Temperature Sensor in the Vascular Endothelium-Enhanced Expressionin SSc Skin and Endothelial Cells Dysfunction After Activation", 3rd Systemic Sclerosis World Congress, Feb. 6-8, 2014, p. S-13.

(Continued)

*Primary Examiner* — Kathrien A Hartsfield
(74) *Attorney, Agent, or Firm* — MacMillan, Sobanski & Todd, LLC

(57) ABSTRACT

Described herein are compositions for, and methods of treating, Raynaud's phenomenon. The compositions comprise a TRPM-8 antagonist formulated in a topical formulation in an amount effective to treat Raynaud's phenomenon.

10 Claims, 27 Drawing Sheets
(23 of 27 Drawing Sheet(s) Filed in Color)

(56) References Cited

OTHER PUBLICATIONS

PCT International Search Report and Written Opinion, Application No. PCT/US16/50500, dated Nov. 18, 2016.

* cited by examiner

TREATMENT OF RAYNAUD'S PHENOMENON BY INHIBITION OF TRANSIENT RECEPTOR POTENTIAL MELASTATIN-8 (TRPM-8)

CROSS-REFERENCE TO RELATED APPLICATIONS

This application This application is a national stage application filed under 35 U.S.C. § 371 of international application PCT/US2016/050500, filed under the authority of the Patent Cooperation Treaty on Sep. 7, 2016, which claims priority to U.S. Provisional Application No. 62/215,529, filed under 35 U.S.C. § 111(b) on Sep. 8, 2015, the entire disclosure of which is expressly incorporated herein by reference.

STATEMENT REGARDING FEDERALLY SPONSORED RESEARCH

This invention not was made with any government support. The government has no rights in this invention.

BACKGROUND OF THE INVENTION

Systemic sclerosis (also known as scleroderma, SSc) is an autoimmune connective tissue disease that is characterized by the presence of Raynaud's phenomenon (RP) that manifests by repeated episodes of vasospasm of the distal arteries upon cold exposure leading to reduced tissue perfusion and hypoxia. It is estimated that over 95% of patients with SSc suffer from Raynaud's phenomenon. The initial trigger (or triggers) that induce SSc is (are) unknown, and the mechanisms responsible for enhanced cold sensitivity in SSc are poorly understood. Cold exposure results in severe vasospasm and reperfusion vascular injury in SSc. The mechanisms responsible for enhanced cold sensitivity in SSc are poorly understood. The fact that Raynaud's phenomenon consistently precedes the onset of clinical disease in the majority of patients with SSc is of great relevance since vascular dysfunction is an early event in SSc pathogenesis.

Raynaud's phenomenon is classified as primary Raynaud's phenomenon in the absence of other vascular or connective tissue disease, or secondary Raynaud's phenomenon if it is associated with connective tissue disease, like systemic sclerosis (SSc, Scleroderma). Raynaud's phenomenon is a common disorder characterized by reversible vasospasm of the extremities induced by cold exposure or emotional stress, which induces paroxysmal episodes of tri-phasic color changes of blanching, cyanosis, and rubor in distal extremities followed by numbness, pain, and often functional disability with a significant impact on the quality of a patient's life. Moreover, Raynaud's phenomenon can be associated with digital ulceration and autoamputation. Primary Raynaud's phenomenon affects up to 11% of women and 8%© of men in the United States. The etiology and pathogenesis of Raynaud's phenomenon is incompletely understood.

Treatment of Raynaud's phenomenon is not satisfactory in general, as current therapy employing calcium channel blockers and other vasodilator agents is either not effective or not well tolerated, due to significant side effects.

In spite of considerable research into therapies to treat this disease, it remains difficult to treat effectively, and the mortality observed in patients indicates that improvements are needed in the diagnosis, treatment, and prevention of this disease.

SUMMARY OF THE INVENTION

In a first broad aspect, there is described herein a topical formulation comprising: a transient receptor potential melastatin-8 (TRPM-8) antagonist composition in an amount sufficient to block TRPM8 activation in skin cells. In certain embodiments, the transient receptor potential melastatin-8 (TRPM-8) antagonist composition comprises econazole and/or clotrimazole, or a salt thereof. In certain embodiments, the TRPM-8 antagonist comprises econazole nitrate. In particular embodiments, the topical formulation includes about 3% w/w econazole nitrate.

In certain embodiments, the topical formulation further comprises hydroxypropyl methylcellulose. In particular embodiments, the hydroxypropyl methylcellulose is present at a concentration ranging from about 0.01% w/w to about 10% w/w. In particular embodiments, the hydroxypropyl methylcellulose is present at a concentration of about 1% w/w.

In certain embodiments, the topical formulation further includes one or more of propyleme glycol, glycerin, DMSO, butylated hydroxyanisole, ethylenediaminetetraacetic acid (EDTA), ethanol, and water.

In certain embodiments, the skin cells comprise microvascular endothelial cells (MVEC), fibroblasts, and vascular smooth muscle cells (VSMC). Further, in certain embodiments, the skin cells comprise Systemic sclerosis (SSc) microvascular endothelial cells (MVEC).

The topical formulation can be in the form of a topical gel, lotion, foam, cream, spray, aerosol, ointment, suspension, emulsion, microemulsion, nanoemulsion, liposomal system, niosomes, solid lipid nanoparticles, lacquer, patch, or bandage.

In a particular embodiment, there is described herein a topical formulation suitable for use in treating Raynaud's phenomenon, where the topical formulation delivers an effective amount of a TRPM-8 antagonist to a region of intact skin over a period of about 2 to 6 hours. Also, the topical gel can further contain at least one cosmetically acceptable humectant, emollient, or softening agent.

In another broad aspect, there is described herein a method for decreasing activities of transient receptor potential melastatin-8 (TRPM-8) in skin cells, comprising: topically administering an effective amount of a compound that blocks TRPM8 activation in skin cells. In certain embodiments, the compound comprises econazole or a salt thereof.

In another broad aspect, there is described herein a method for decreasing the expression of endotheline-1 (ET1) in skin cells, comprising: topically administering an effective amount of a compound that blocks TRPM8 activation in skin cells. In certain embodiments, the compound comprises econazole or a salt thereof.

In another broad aspect, there is described herein a method of increasing the expression of endothelial nitric oxide synthase (NOS3) and prostacyclin synthase (PTGIS) mRNA expression in skin cells, comprising: topically administering an effective amount of a compound that blocks TRPM8 activation in skin cells. In certain embodiments, the compound comprises econazole or a salt thereof.

In another broad aspect, there is described herein a method of treating cold-induced vascular dysfunction, comprising topically administering to skin cells an effective amount of a TRPM-8 antagonist sufficient to decrease expression of TRPM-8. In certain embodiments, the TRPM-8 antagonist comprises econazole or a salt thereof.

In another broad aspect, there is described herein a method of blocking TRPM8 activation as a therapeutic strategy in SSc cold-induced vascular spasm, comprising: topically administering an effective amount of a compound that blocks TRPM8 activation in skin cells. In certain embodiments, the compound comprises econazole or a salt thereof.

In another broad aspect, there is described herein a method of treating Raynaud's phenomenon and/or pain from exposure to cold, comprising the steps of: identifying a subject suffering from Raynaud's phenomenon and/or pain from exposure to cold; and, topically administering to the subject a pharmaceutical composition comprising a pharmaceutically acceptable carrier and a TRPM-8 antagonist, or a pharmaceutically acceptable salt thereof, in an amount effective to treat Raynaud's phenomenon and/or pain from exposure to cold. The pain can be associated with fingers, hands, toes, or feet. In certain embodiments, the TRPM-8 antagonist comprises econazole or a salt thereof.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 7A shows an image of active vasospasm. FIG. 7B shows an image of spontaneous improvement in blood flow. FIG. 7C shows an image of hyperemia. FIG. 7D shows an image taken 5 minutes after a cold challenge test, which was performed by immersing a gloved left hand in 15° C. water. Blue-yellow regions indicate areas of lower perfusion. FIG. 7E and FIG. 7F demonstrate corresponding photoplethysmography (PPG) changes at right and left index fingers, respectively, in response to the cold challenge to the left hand.

DETAILED DESCRIPTION

Figure 1A:
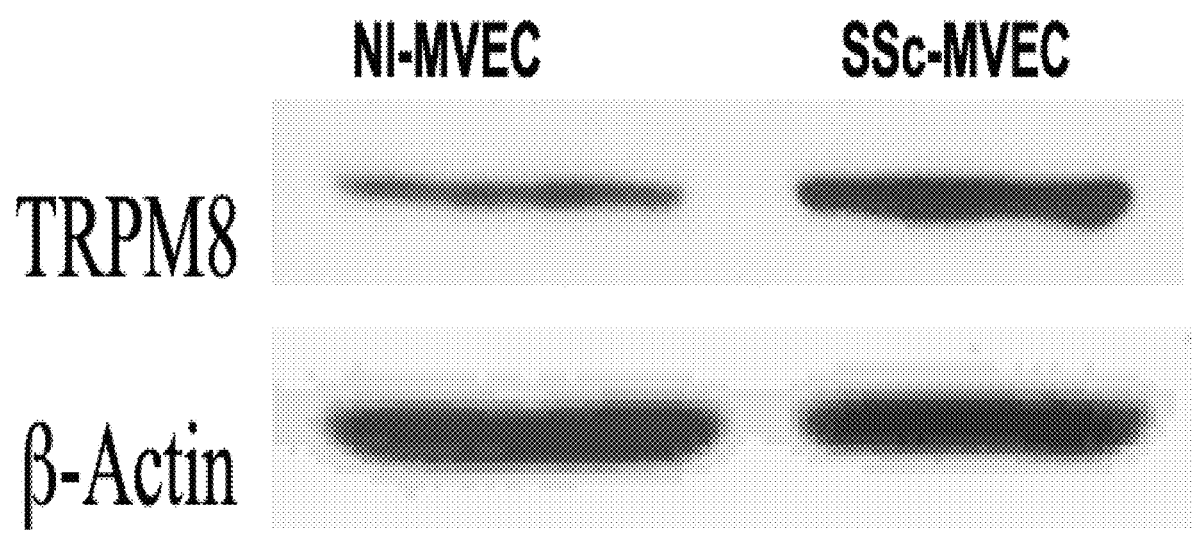
FIGS. 1A-1C: Evaluation of mRNA expression of TRPM8 in normal MVEC and SSc-MVEC (FIG. 1A). TRPM8 expression in SSc MVEC was around 2.7 fold higher than normal MVEC (FIG. 1B). Upregulation of TRPM8 was detected by RTqPCR and by immunohistochemistry and western blot. TRPM8 mRNA expression levels were significantly increased in SSc-MVEC (2.6 fold±0.22 vs. control MVEC) and SSc-skin biopsies (10.5 fold±2.3 vs. control skin biopsies) (FIG. 1C).

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Definitions

As used herein, the term "treating" a medical condition encompasses therapeutically regulating, preventing, improving, alleviating the symptoms of, reducing the effects of, and/or diagnosing, the medical condition. As used herein, the term "medical condition" encompasses any condition, disease, disorder, function, abnormality, or deficit influenced by cold exposure. Further, the methods of the present disclosure can be used to treat more than one medical condition concurrently. The term "reducing the symptoms" refers to reducing either or both of the incidence or severity of symptoms.

General Description

The Transient Receptor Potential (TRP) ion channels are a family of proteins that function as detectors of thermal and chemical stimuli that activate sensory neurons. Transient Receptor Potential Melastatin 8 (TRPM8) is one of the TRP proteins in the family, and is a calcium-permeable non-selective cation channel protein that is directly activated by cold temperatures below 26° C. Without wishing to be bound by theory, TRPM8 is now believed to be the main molecular transducer entity responsible for the sensitivity to innocuous cold. TRPM8 is expressed in peripheral sensory neurons, in skeletal and smooth muscle, and in the epithelium prostate, lungs, bladder, and urogenital tract. Also, TRPM8 is believed to be expressed in a number of vascular beds, including rat aorta, mesenteric artery, femoral artery, and rat tail artery. However, the role of TRPM8 channels in the regulation of vascular tone remains unclear.

One method for the non-invasive evaluation of Raynaud's phenomenon is photoplethysmography (PPG), which involves using infrared light for transcutaneous recording of blood volume changes in the skin vessels. Another method is infrared thermography, which is a technology that relies on evaluating the difference of skin temperature as a tool for dynamic evaluation of digital blood flow by creating temperature maps. Infrared thermography is useful as a tool to evaluate Raynaud's phenomenon and assess response to therapeutic interventions, and is believed to be a sensitive test with high reproducibility.

Infrared thermography is a useful non-invasive test to objectively evaluate Raynaud's phenomenon since infrared thermography correlates with digital blood flow at baseline and after a cold challenge test. Overall, infrared thermography is a useful method not only to illustrate distribution of skin temperature, but also to indirectly measure for skin perfusion. Due to the good correlation between infrared thermography and perfusion measurements, and its quick and easy applicability, infrared thermography is considered cost- and time-saving to use for the monitoring of perfusion changes in patients with Raynaud's phenomenon. For the sake of comparison, two modalities were used in the Examples herein to assess outcome of treatment using different TRPM8 antagonists: infrared thermography and PPG.

Described herein are methods and compositions useful for mediating the expression of TRMP8 in SSc and healthy control MVEC and skin. In some embodiments, the compositions are topical compositions. Topical or transdermal delivery systems for the administration of drugs offer several advantages over oral delivery of the same drugs. Generally, the advantages of topical or transdermal delivery of drugs relate to pharmacokinetics. For example, one problem associated with the oral delivery of drugs is the occurrence of peaks in concentration levels of the drug, which is followed by a drop in concentration levels of the drug due to its metabolism and elimination. Thus, the concentration levels of orally administered drugs have peaks and valleys after ingestion. These highs and lows in concentrations of drug often lead to undesirable side effects.

In contrast, topical and transdermal delivery of drugs provides a relatively slow and steady delivery of the drugs. Unlike orally administered drugs, the concentrations of topically or transdermally delivered drugs are substantially sustained and do not have the peaks associated with oral delivery. Compared with oral delivery, topical administration leads to high dermal concentration of drugs with minimal or no side effects.

One embodiment of a topical formulation provided herein is a 3% (w/w) econazole nitrate formulation that is a hydroxypropyl methylcellulose (HPMC) dispersion. This formulation, referred to herein as a 3% econazole nitrate HPMC dispersion, generally exhibits a loosely structured translucent gel consistency. The HPMC is generally present at a concentration ranging from about 0.01% (w/w) to about 10% (w/w), or from about 0.5% (w/w) to about 5% (w/w), or from about 0.8% (w/w) to about 1.5% (w/w). In one non-limiting example, the HPMC is present at a concentration of about 1% w/w. The formulation may further include one or more of propylene glycol, glycerin, DMSO, butylated hydroxyanisole, ethylenediaminetetraacetic acid (EDTA), ethanol, and water.

The 3% econazole nitrate HPMC dispersion has superior penetration through skin layers compared to commercially available econazole. In particular, as shown in the Examples herein, this formulation shows about a 50-fold higher permeation into stratum corneum, epidermis, and dermis skin layers compared to a commercially available econazole formulation. The 3% econazole nitrate HPMC dispersion also achieves a higher concentration of econazole nitrate in the stratum corneum, epidermis, and dermis layers.

The formulations provided herein can further include at least one of a gelling agent, neutralizing agent, buffering agent, moisturizing agent, humectant, surfactant, antioxidant, preservative, emollient, film-forming agent, or buffer, and the like.

The formulations may be applied directly to the skin such as by, for example and not limitation, a gel, a foam, an ointment, a liposomal emulsion, a microemulsion, a nanoemulsion, a suspension, a gel containing solid lipid nanoparticles, a gel containing niosome or a lacquer and the like, or other passive or active transdermal devices for absorption through the skin or mucosal surface. In a preferred aspect of the present disclosure, the formulation is a gel.

Use of a long-term sustained release patch may be desirable. Long-term release, as used herein, means that the patch is constructed and arranged to deliver therapeutic levels of the active ingredient for at least 1-2 days, and preferably 1-7 days. Long-term sustained release patches are known to those of ordinary skill in the art and include some of the release systems described above.

The present disclosure also includes various kits. Each of the kits includes a jar, tube, bottle, foil pouch, patch, or other container for holding a pharmaceutical preparation containing, as an active ingredient, a chemical compound for reducing the severity and/or incidence of symptoms of Raynaud's phenomenon, and instructions for dispensing an amount of the pharmaceutical preparation effective to reduce symptoms of Raynaud's phenomenon. Alternatively, the kit may contain the chemical compound and a pharmaceutically acceptable carrier in separate containers, the contents of which are combined prior to administration.

Preferably, the pharmaceutical preparation is in the form of a topical preparation, either constructed and arranged to deliver an appropriate or effective amount of the chemical compound, or with a dispensing means permitting dispensing of appropriate amounts of the compound. A topical preparation containing the chemical compound (i.e., a TRPM-8 antagonist or salt thereof) may be in the form of a cream, a lotion, an ointment, a gel, or other known forms for topical administration. If desired, the topical preparation may be contained in individual packets, each packet containing an appropriate dose for topical application. The kit may include a plurality of such packets, such as 30, 60, 100, or more packets, each packet containing an amount of cream that may be conveniently rubbed into a single location on the skin of a user, typically about 1-2 ml of the topical preparation.

Such cream, lotion, ointment, gel, or other form for topical administration may be administered such as by application, with or without rubbing, to the skin. One preferred location of administration is to the upper surface of the foot. Other examples of preferred locations for topical administration are to the skin of the face and of the hands and forearms.

All publications, including patents and non-patent literature, referred to in this specification are expressly incorporated by reference herein. Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

EXAMPLES

Example 1

The overexpression of TRPM8 in scleroderma mediates the cold sensitivity in Raynaud's phenomenon and in SSc and antagonizing TRPM8 is a useful therapeutic modality. In vitro studies show the efficacy of inhibition of TRPM8 in MVEC culture. There is upregulation of TRPM8 in MVEC from patients with SSc. The activation of TRMP8 receptors leads to reduced nitric oxide synthase (NOS3) and prostacyclin synthetase (PTGIS), and enhanced endothelin 1 (ET1) gene expressions, and inhibition of TRPM8 by capsazepine leads to normalization of gene expression levels. Thus, TRPM8 antagonists are useful as a therapeutic modality in Raynaud's phenomenon.

Up Regulation of TRPM8 in SSc-MVECs

Figure 1B:
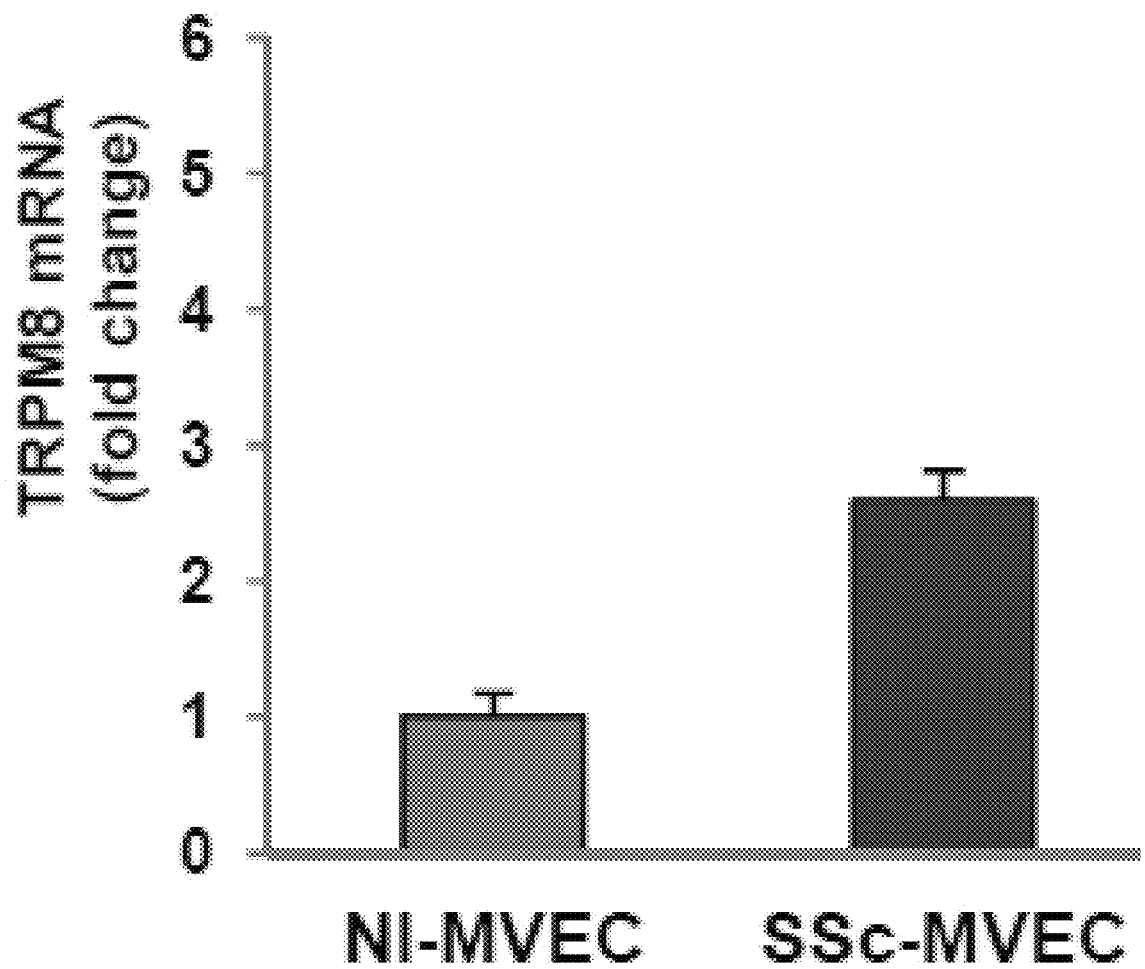
Figure 1C:
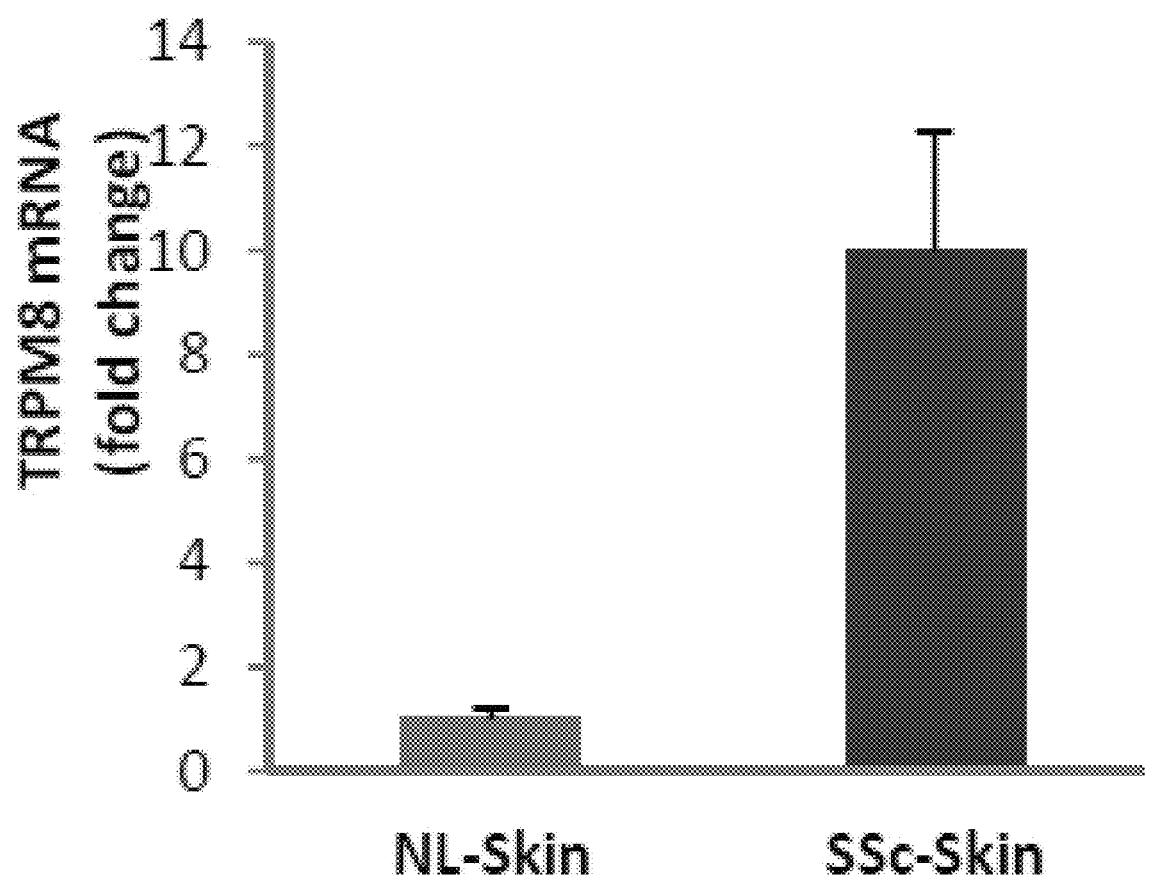

The expression levels of TRPM8 receptor in SSc-MVEC compared to controls, as well as total skin tissue biopsy from patients with SSc, were evaluated by RT-qPCR, immunohistochemistry, and by western blot analysis. FIGS. 1A-1C show significant upregulation of TRPM8 expression levels not only in SSc-MVEC, but also in SSc skin biopsies compared to controls. This indicates that there are other cell types that may be involved also by upregulation of TRPM8, such as vascular smooth muscle cells (VSMC) and fibroblasts.

Increased Intracellular Calcium in Response to TRPM8 Agonists in MVEC

Figure 2:
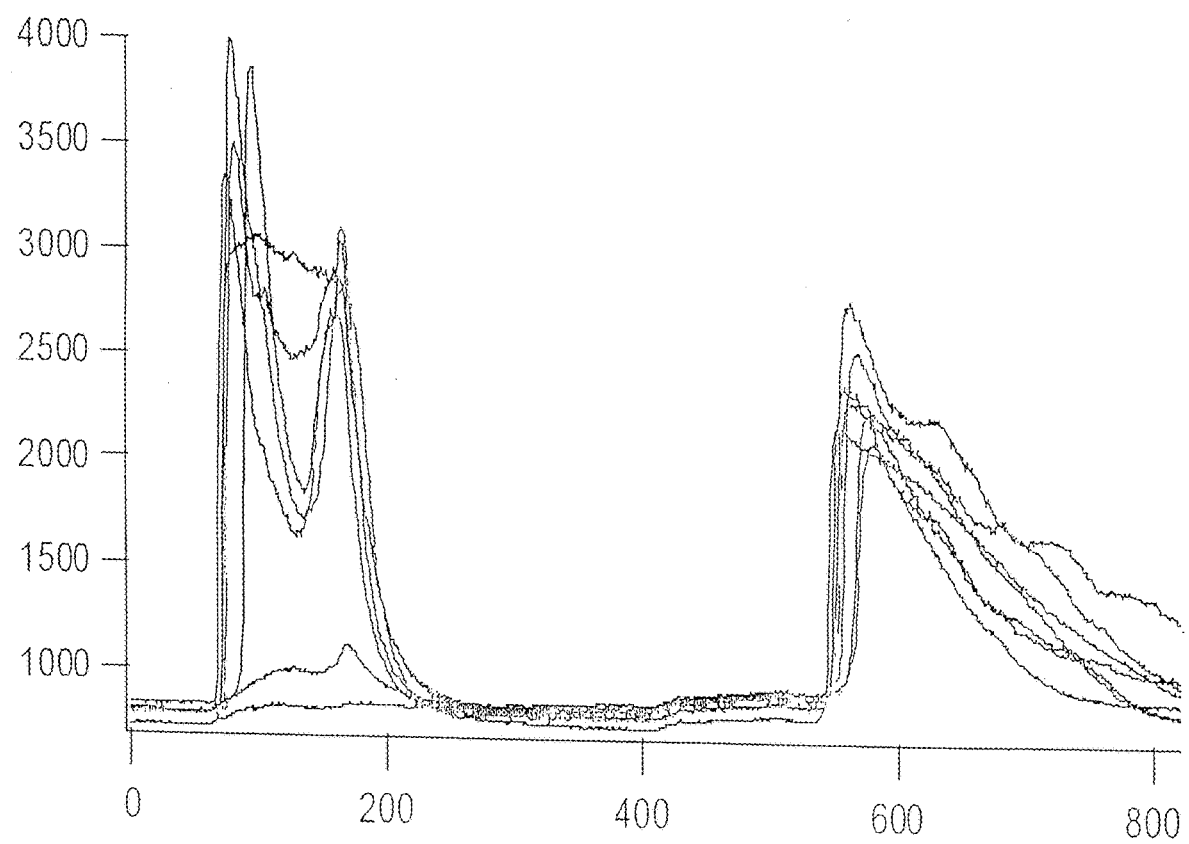
FIG. 2: Pharmacological activation of TRPM8 in human microvascular endothelial cells. An increase in $Ca^{2+}$ influx in MVEC was observed in response to 500 µM/L menthol. ATP was used as the positive control.

To evaluate the functional role of TRPM8 in MVECs, the intracellular calcium ($[Ca^{2+}]$) influx into MVEC by $Ca^{2+}$ was evaluated by microfluorometry studies in response to the addition of menthol or exposure to cold, which are known to activate TRPM8 (FIG. 2).

Figure 3:
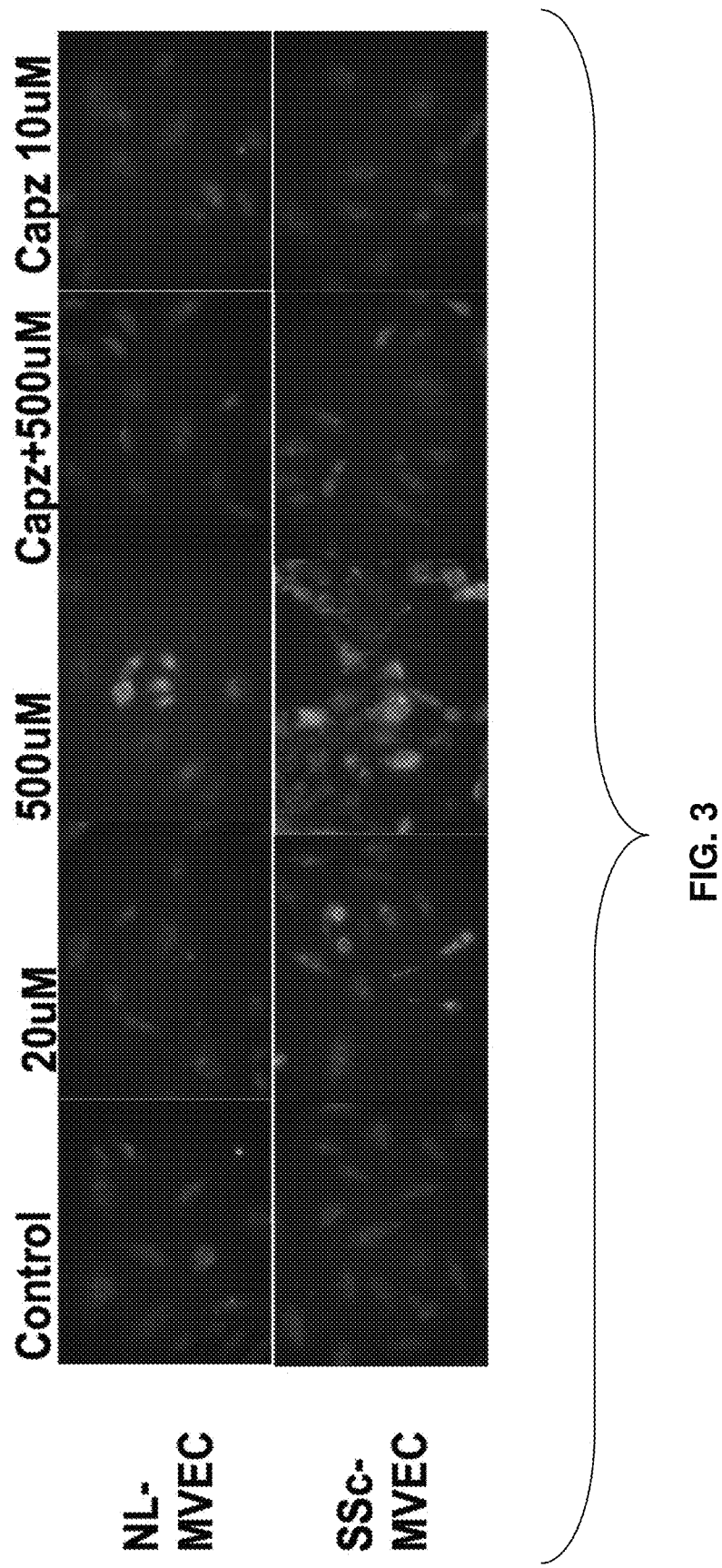
FIG. 3: Effects of menthol on intracellular calcium level in NL-MVECs and SSc-MVECs. Cells were loaded with 2 µM calcium indicator dye Fluo-4AM for 1 hour and treated with menthol with and without capsazepine for 10 minutes and then observed under microscope.

Further, FIG. 3 demonstrates that menthol increases intracellular calcium levels in both SSc MVEC and healthy MVEC. The effect of menthol is abrogated by the use of Capsazepine, a TRPM8 receptor inhibitor. These findings indicate that TRPM8 mediates functional effects in MVEC that are mediated by calcium influx, which is antagonized by the use of Capsazepine.

Effect of TRPM8 Activation on MVEC Gene Expression

The effects of TRPM8 activation by cold exposure or menthol on MVEC gene expression were evaluated. TRPM8 activation leads to an increase in Endothelin-1 (ET-1) expression, which is one of the most potent vasoconstrictive molecules that is also upregulated in SSc, and a decrease in Nitric Oxide Synthase 3 (NOS3) expression levels, which is an important enzyme that is involved in nitric oxide production by MVEC. Therefore, TRPM8 activation leads to aberrant expression levels of key MVEC genes that may be involved in MVEC dysfunction.

Effect of TRPM8 Agonists and Antagonist on Endothelial Genes

Figure 4A:
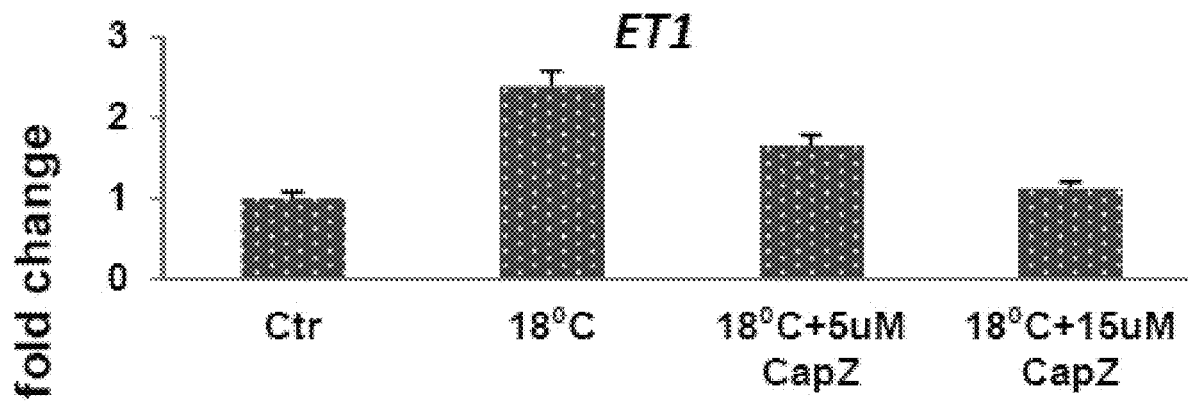
FIGS. 4A-4C: Effects of cold exposure on ET1 (FIG. 4A), NOS3 (FIG. 4B), and PTGIS (FIG. 4C) mRNA expression. Normal MVECs were exposed to 18° C. temperature for 1 hr. The mRNA expression levels were measured by qPCR.
Figure 4B:
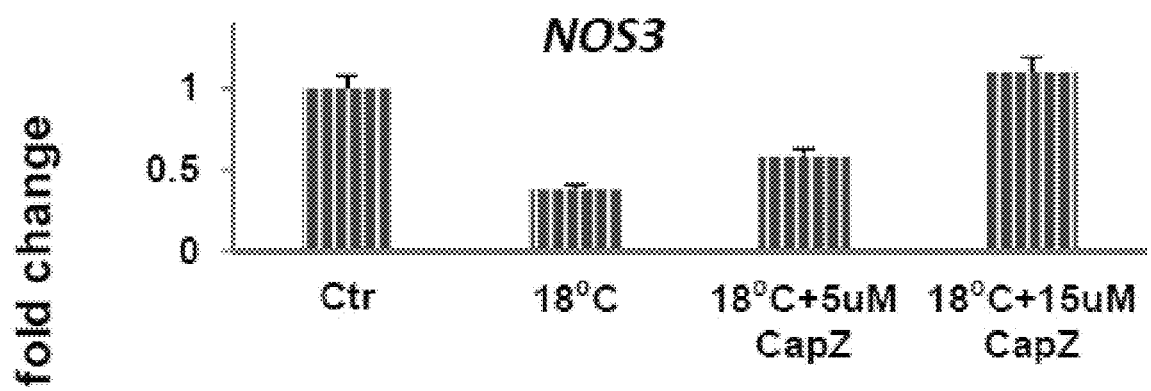
Figure 4C:
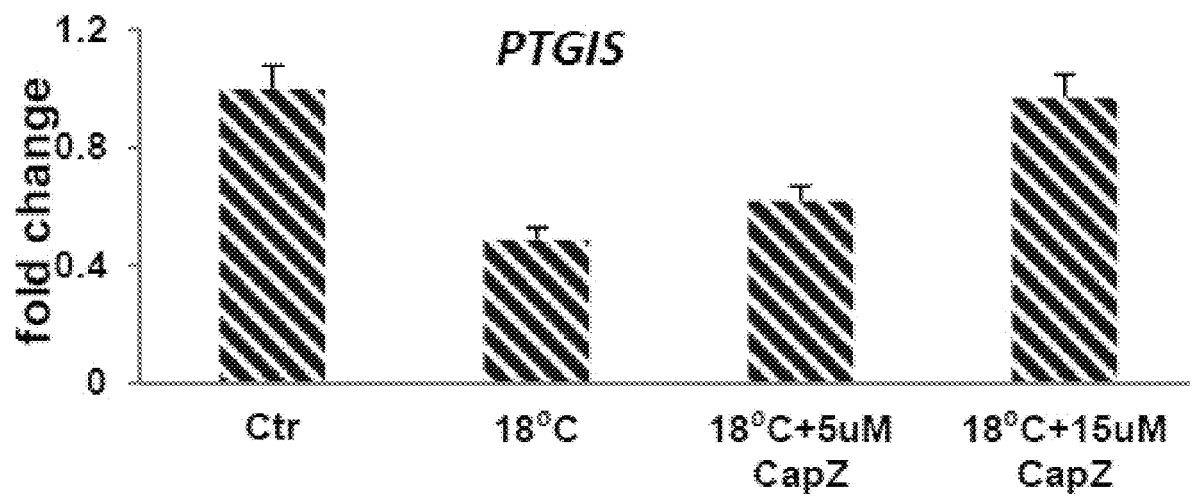
Figure 5A:
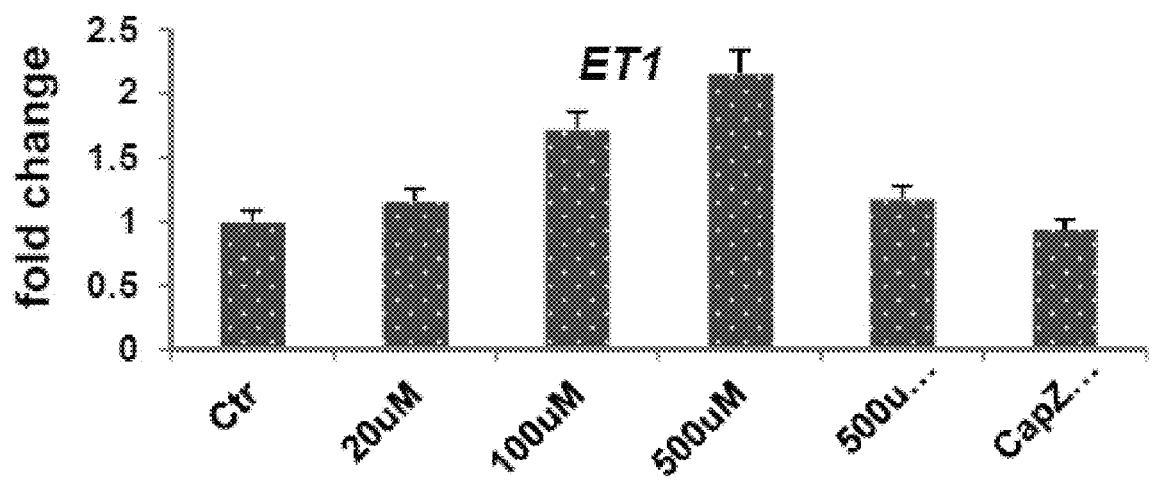
FIGS. 5A-5C: Effects of Menthol on ET1 (FIG. 5A), NOS3 (FIG. 5B), and PTGIS (FIG. 5C) mRNA expression. Normal endothelial cells were treated with menthol (MT) at 20 µM, 100 µM, and 500 µM with and without capsazepine (CapZ) for 24 hours. The mRNA expression levels were measured by qPCR.
Figure 5B:
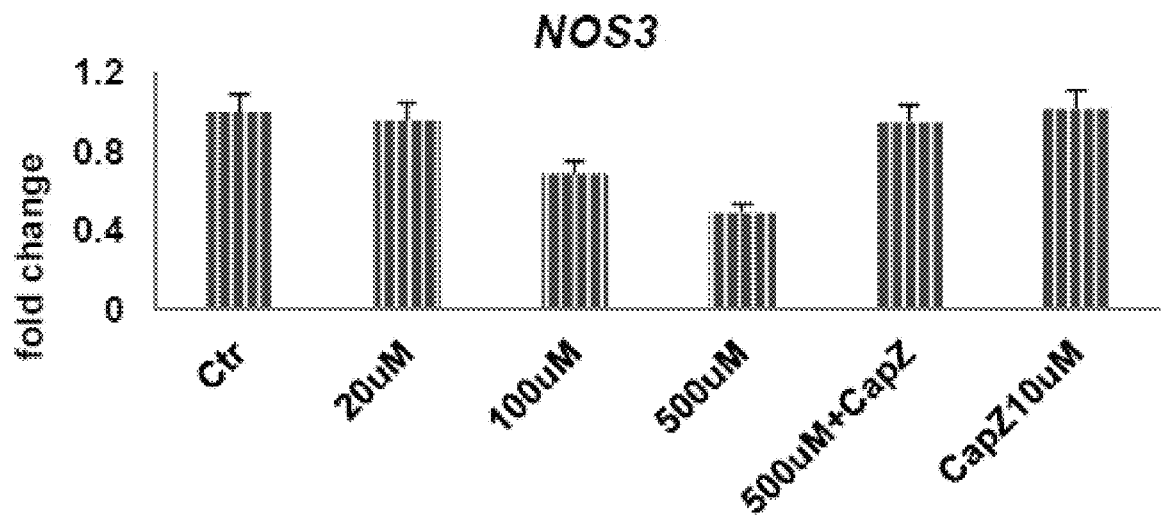
Figure 5C:
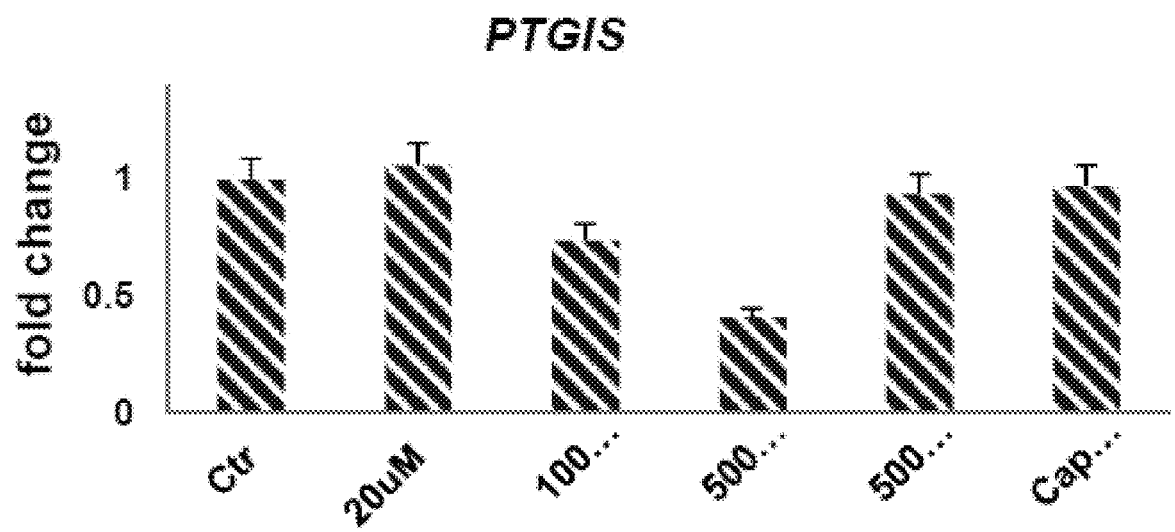

The effect of exposure of normal MVEC to TRPM8 antagonists on MVEC gene expression was evaluated. Specifically, gene expression levels of NOS3, PTGIS, and ET1 in MVEC were evaluated in response to TRPM8 activation by cold exposure (FIGS. 4A-4C) and menthol (FIGS. 5A-5C) with and without Capsazepine, which is one of the TRPM8 receptor inhibitors.

Activation of TRPM8 in MVEC by cold temperature or by menthol significantly increased the expression of ET1 (2.4 folds±0.21) and decreased NOS3 (62%±5.1 reduction) and PTGIS (61%±4.8) expression levels. Notably, these effects were reversed by the addition of the TRPM8 antagonist capsazepine. These data indicate that TRMP8 is involved in cold-induced vascular dysfunction, in view of heightened expression levels in SSc-MVECs and effects of activation on generation of MVEC dysfunction. Thus, the use of TRPM8 antagonists can be an effective strategy for treatment Raynaud's phenomenon in SSc patients.

Topical Gel Formulation of Capsazepine and Chromatographic Conditions of Capsazepine A poloxamer solution (20% w/v) was prepared using the cold method. The poloxamer solution was stored under refrigerated conditions at 4° C. overnight in order to enhance the dissolution of the polymer. Butylated hydroxytoluene (BHT) was used as an antioxidant at a concentration of 0.1% w/w. Capsazepine (3% w/v) and BHT (0.1% w/v) was dissolved in a required amount of propylene glycol. The final formulation was prepared by mixing the poloxamer solution with propylene glycol solution in 1:1 ratio.

Figure 6:
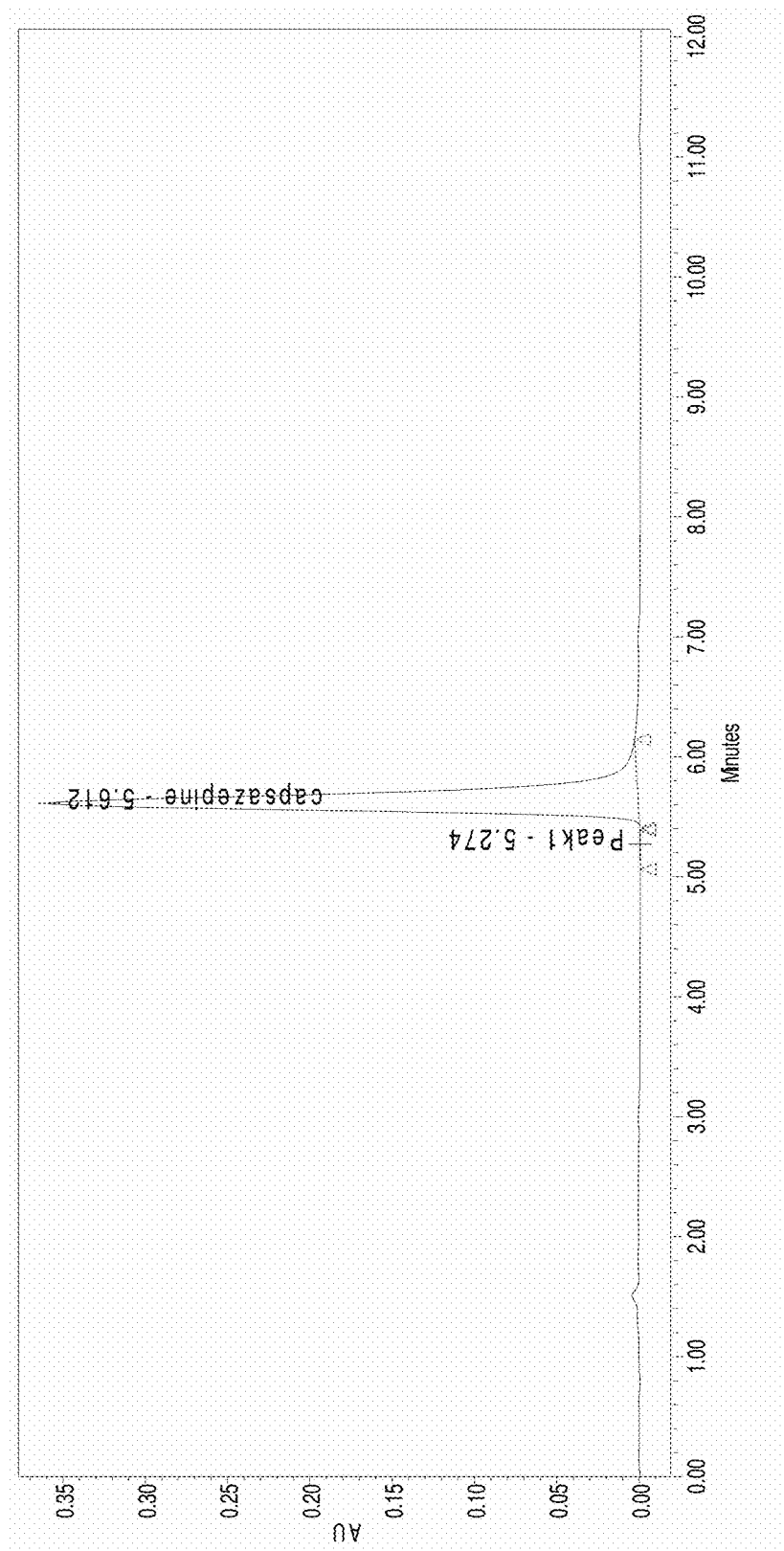
FIG. 6: Sample HPLC chromatogram of capsazepine.
Figure 7A:
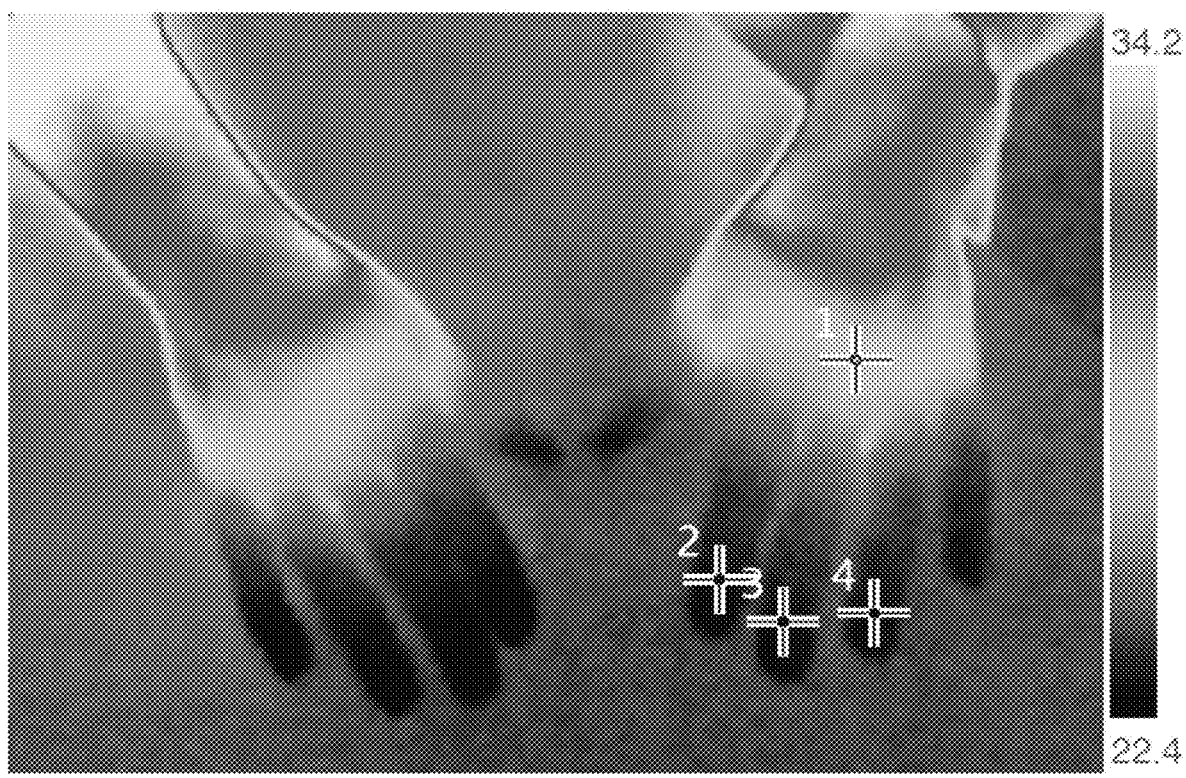
FIGS. 7A-7F: An illustrative example of dynamic changes in vascular perfusion that are detected by infrared thermography and photoplethysmography (PPG).
Figure 7B:
Figure 7C:
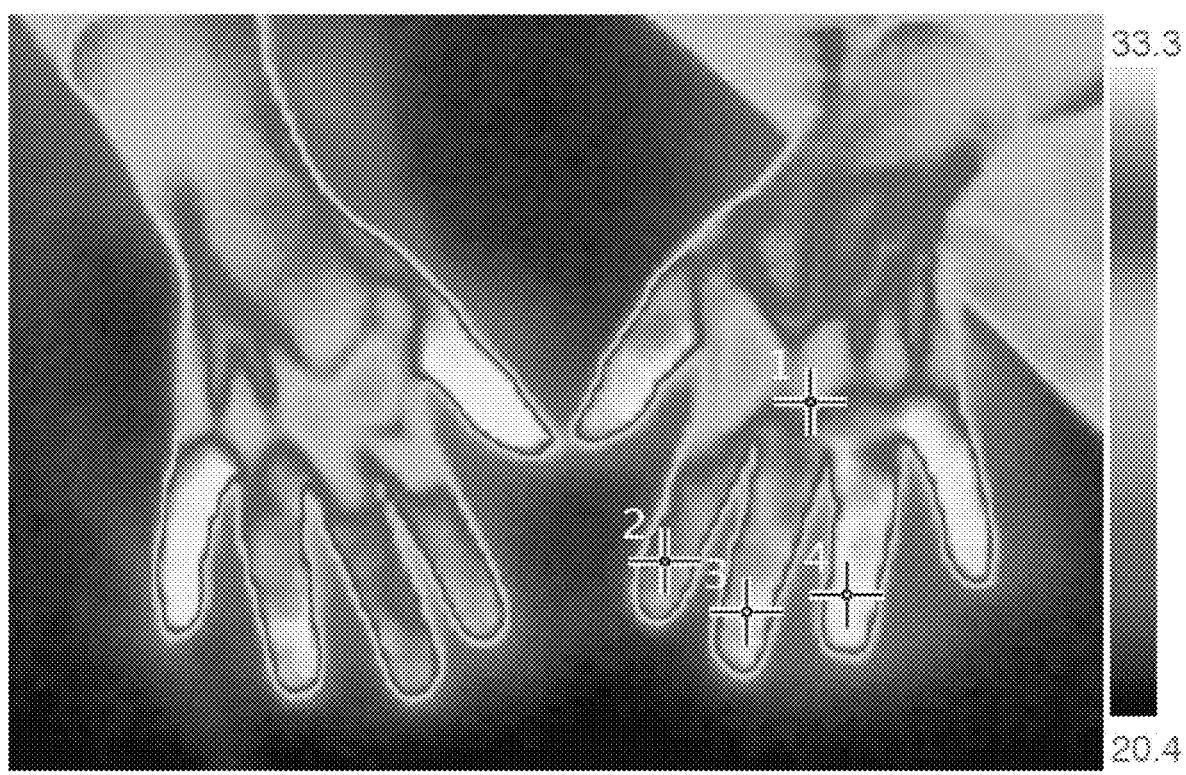
Figure 7D:
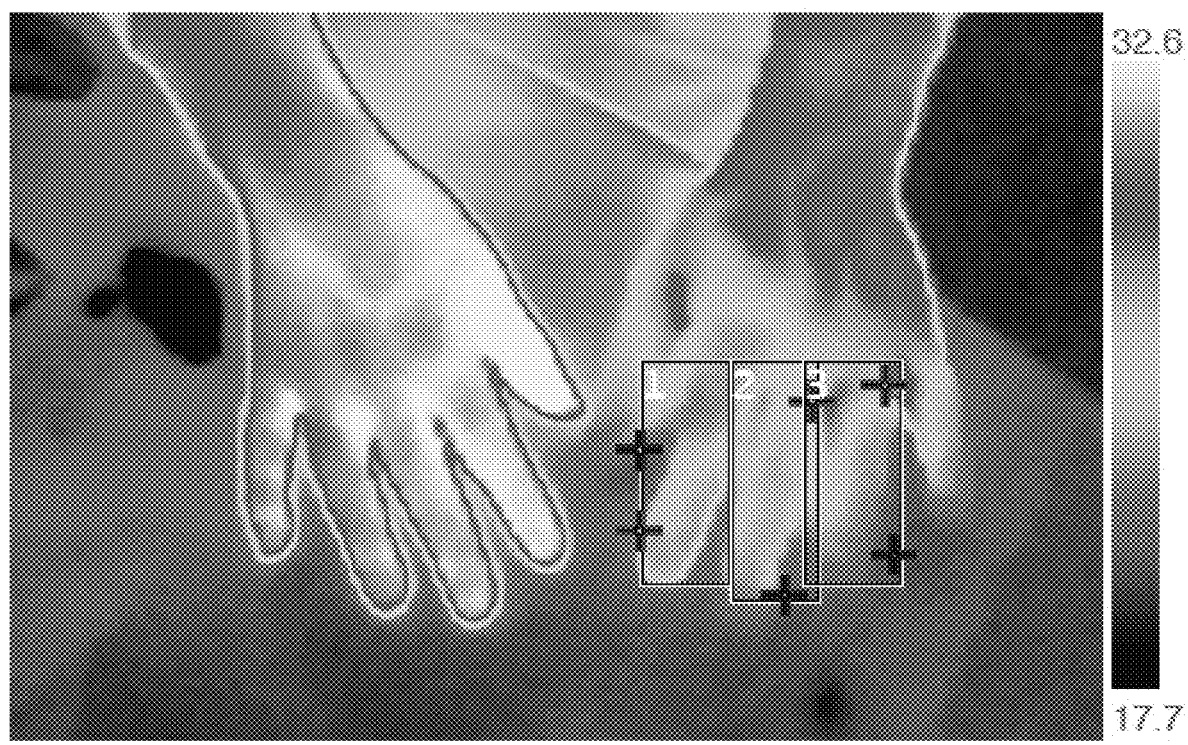
Figure 7E:
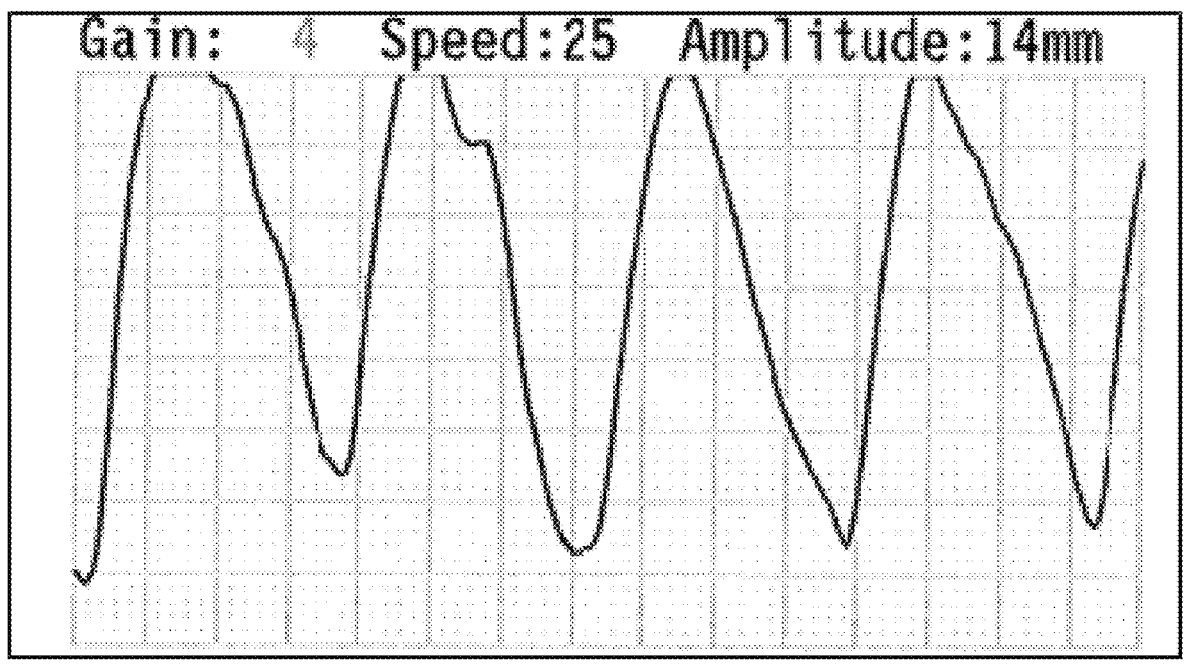
Figure 7F:
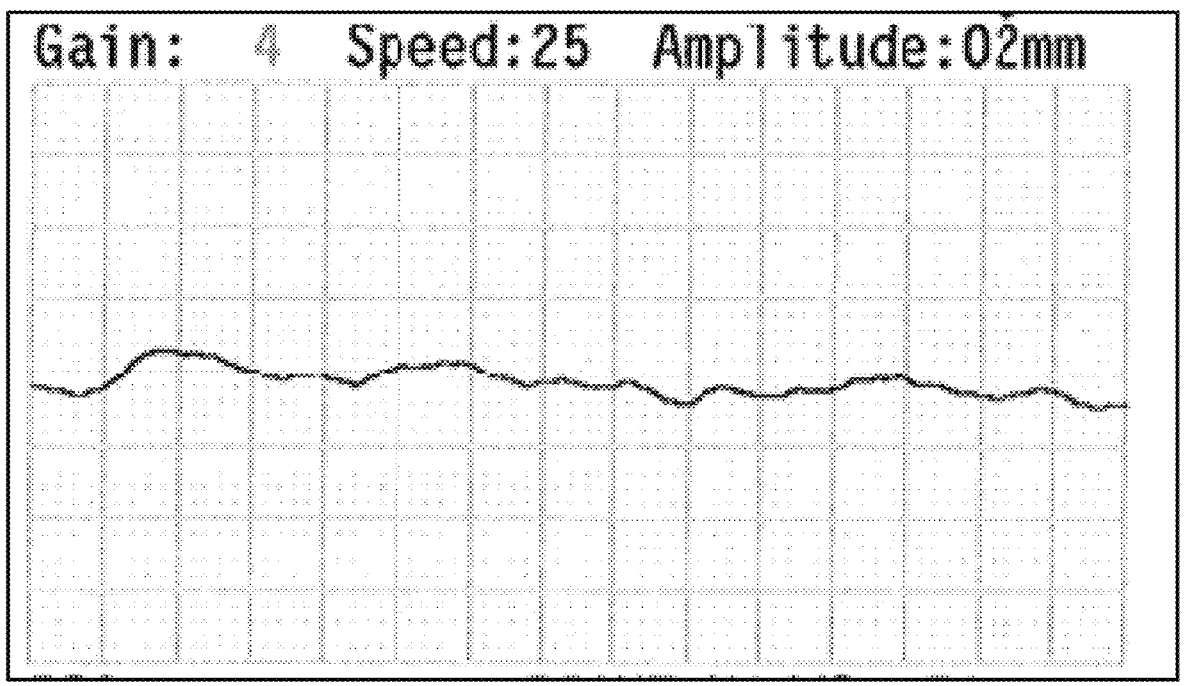

To determine the chemical properties of capsazepine, and to show the usefulness of using capsazepine as a therapeutic compound to prevent vasospasm induced by cold exposure, a topical gel formulation of capsazepine was prepared for application in humans. Drug content of the capsazepine was analyzed by using a high-performance liquid chromatography system (HPLC) (Waters Alliance e2695 separation module, Milford, Mass.), equipped with a 2998 PDA detector. Samples were analyzed using a reverse-phase C18 column (5 μm, 100 A, Microsrob, Woburn, Mass., USA) with a mobile phase composed of acetonitrile: water (60:40) pumped at a flow rate of 1 mL/min. The retention time capsazepine (λnax=286 nm) was found to be 5.612 minutes (FIG. 6).

The drug content was determined quantitatively by plotting a calibration curve. A stock solution 1 mg/mL of capsazepine was used in preparing the calibration curve standards. Various calibration concentration standards of capsazepine were prepared ranging from 0.078 μg/mL-10 μg/mL, in the mobile phase. For the calibration curve, each standard concentration was analyzed in triplicate and the average peak area was plotted against concentration. The assay method was found to be linear with a correlation coefficient of 0.9997. The percentage recovery of capsazepine ranged from 97.2% to 105.8%. The intra- and inter-assay precisions of capsazepine were satisfactory; the relative standard deviations did not exceed 2%. The limit of detection and limit of quantification of capsazepine was found to be 46.9 ng/ml and 153.3 ng/ml, respectively.

Preparation of Econazole or Clotrimazole Loaded PLO Gels

PLO gels of econazole or clotrimazole were prepared using a cold method, where an oil phase can be prepared by mixing lecithin and ricinoleic acid in 1:1 ratio. The mixture was allowed to stand overnight to allow for the complete dissolution of lecithin in the ricinoleic acid. Poloxamer solution (20% w/v) was prepared using the cold method, as mentioned above. Required amounts of econazole or clotrimazole were dissolved in the mixture of lecithin and ricinoleic acid. BHT (0.1% w/v) was also dissolved in the oil phase containing econazole or clotrimazole. PLO gel was prepared by mixing oil phase (mixture of lecithin and ricinoleic acid) and aqueous phase (20% w/v poloxamer 407 solution) using a vortex mixer (VORTEX—T, Genie® 2). Drug loaded PLO gels were evaluated for pH, viscosity, drug content, morphology, and stability.

Determination of pH

For the determination of pH, 1 g of formulation was dispersed in 25 ml of distilled deionized water, and the pH was determined using an Accumet® excel XL 25 pH meter (Fisher Scientific, Pittsburgh, Pa.). The pH meter was calibrated with standard buffer solutions of pH 4, 7, 10 before each use.

Determination of Viscosity

A Brookfield HBDV-III+ Ultra Cone/Plate Rheometer (Brookfield Engineering Laboratories, Middleboro, Mass.) was used with a CPA-52X Cone Spindle to determine the viscosities. Tests were performed at 25° C., and the temperature was controlled by using a Brookfield Programmable Bath, type TC-550MX-115 (Brookfield Eng. Lab., Middleboro, Mass.). The viscosities of formulations were measured at varying shear rates (e.g., 10, 40, 70, 100 sec$^{-1}$).

Drug Content

The drug content was analyzed using a high-performance liquid chromatography system (HPLC) (Waters Alliance e2695 separation module, Milford, Mass.), equipped with a 2998 PDA detector. Capsazepine was measured using a Waters C18 column (75×4.6 mm, Symmetry®) with a mobile phase composed of acetonitrile and water (60:40), pumped at a flow rate of 1 ml/min. Absorbance of capsazepine was measured at 286 nm. For econazole, a Lux® 5 Cellulose-2, LC Column (250×4.6 mm) was used with a mobile phase composed of hexane/isopropyl alcohol (60:40) (diethanolamine 0.1%) pumped at a flow rate of 1 ml/min. Absorbance of econazole was measured at 220 nm. Clotrimazole was measured using a Waters C18 column (75×4.6 mm, Symmetry®) maintained at 40° C. A mobile phase composed of acetonitrile and 0.005M ammonium acetate (pH=7.6) (65:35) was pumped at a flow rate of 1 ml/min. Clotrimazole peaks were monitored at a wavelength of 210 nm.

Morphology

Scanning Transmission Electron Microscopy (Hitachi HD-2300A) was used for studying the morphology of formulations. Samples were prepared by placing a small amount of gel on a carbon-coated copper grid, and the samples were freeze dried using a Labconco Benchtop FreeZone freeze dryer. The freeze dried samples were stained with 1% phosphotungstic acid solution, and images were captured with a Transmission electron microscopy after the sample was completely dried.

Stability Study

Stability of capsazepine formulation was evaluated at −20° C. The stability of econazole and clotrimazole was evaluated at 25° C./60% RH and 40° C./75% RH, respectively. Stability samples were analyzed for drug content using high-performance liquid chromatography at regular time intervals for up to 6 months.

Assessment of Digital Blood Flow in Response to Cold Challenge Test

A FLIR thermography system (Wilsonville, Oreg.) was used to evaluate blood flow in the digits in response to a cold challenge test in addition to PPG. The advantage of combining the two modalities is that both (i) a dynamic assessment of blood flow in the hands as reflected by changes in temperature in response to cold challenge tests, as well as (ii) the ability to obtain single point measurements, can be achieved.

FIGS. 7A-7F show the dynamic changes in blood flow as detected by thermal images during the three phases of active Raynaud's phenomenon that were partially reproduced by the cold challenge test.

Figure 8A:
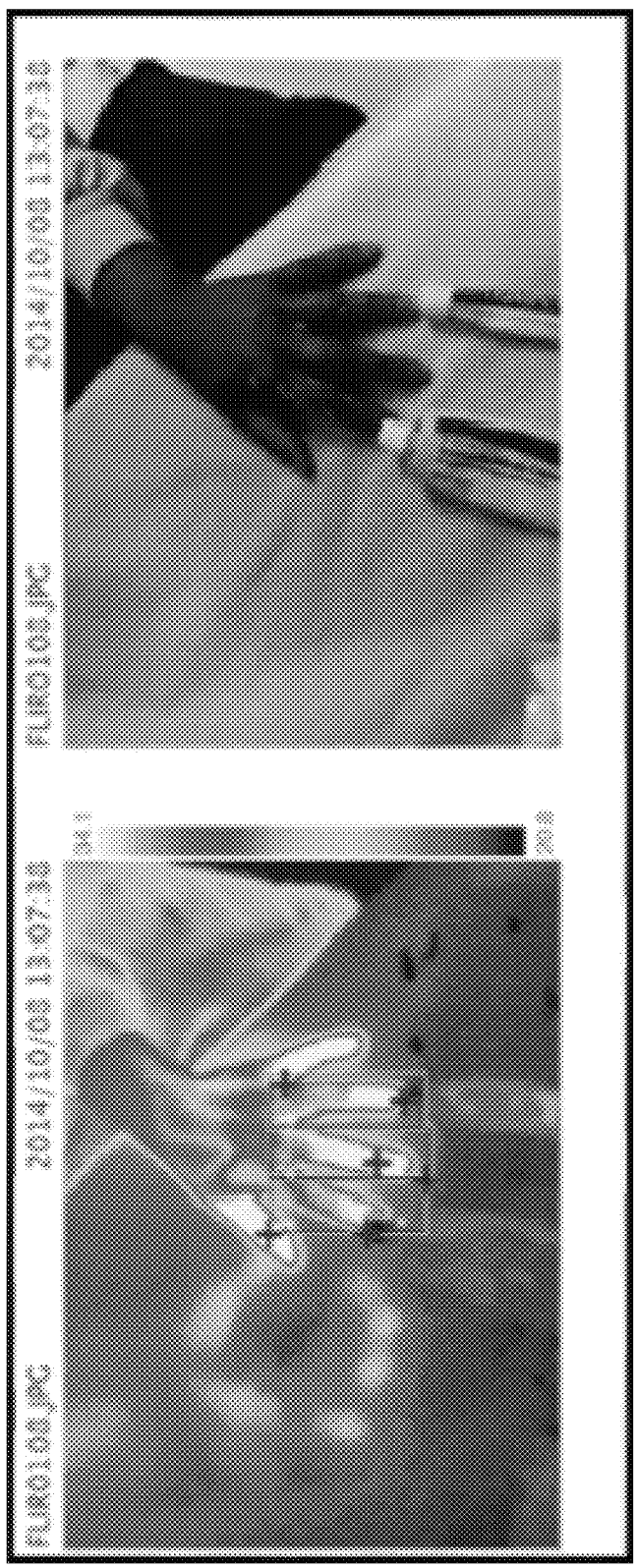
FIG. 8A: Image showing local application of econazole to the left index finger, and clotrimazole to the ring finger for 15 minutes before cold exposure.
Figure 8B:
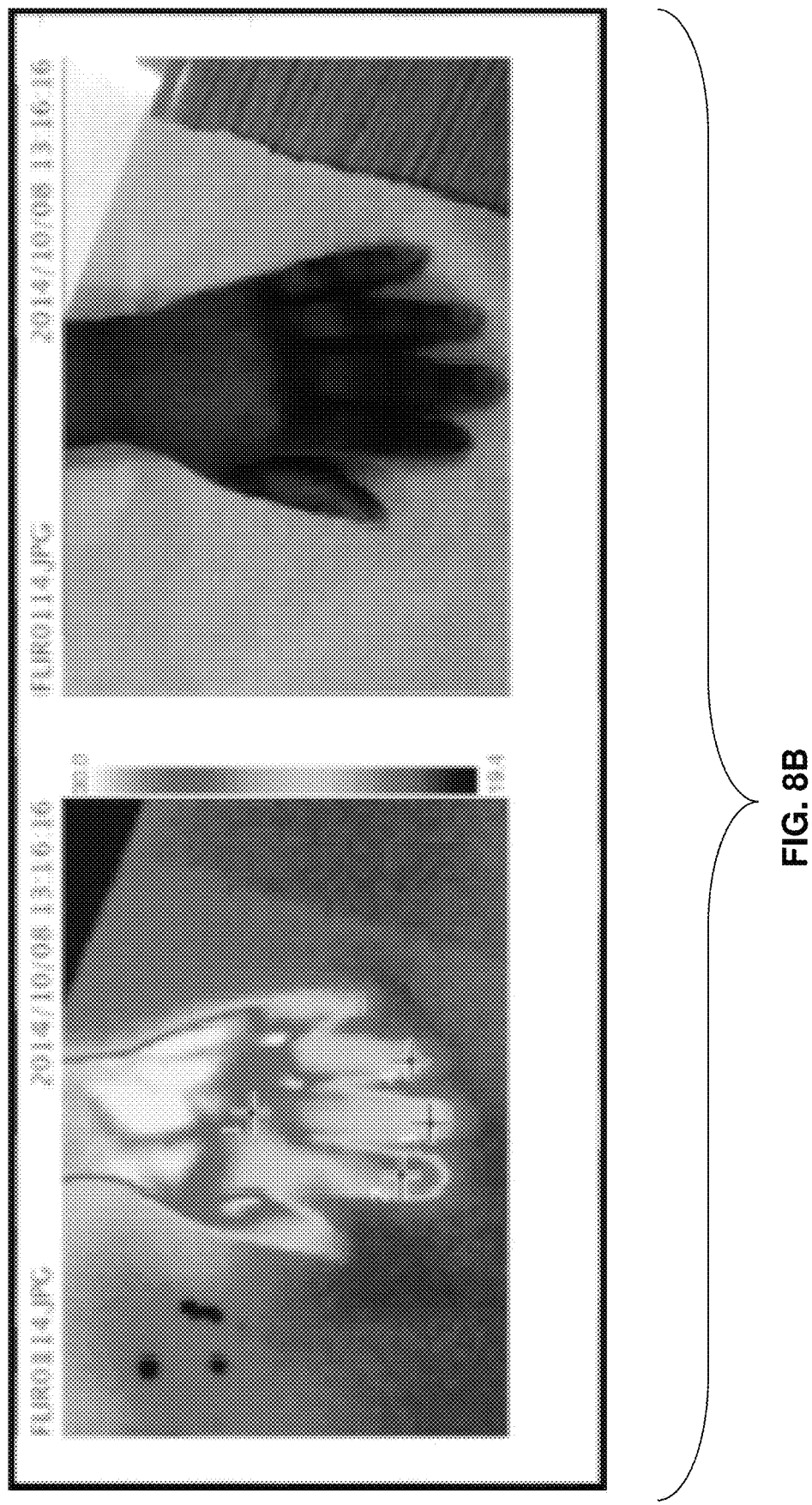
FIG. 8B: Image demonstrating that the left index finger (where econazole was applied) is warmer than the other fingers.

FIGS. 8A-8B show the local application of econazole to the left index finger, and clotrimazole to the ring finger, for 15 minutes before cold exposure (FIG. 8A). FIG. 8B shows an image that demonstrates that the left index finger (where econazole was applied) is warmer than the other fingers. Note the red color that depicts higher temperature of skin on the left index finger in the right panel of FIG. 8B.

Figure 9:
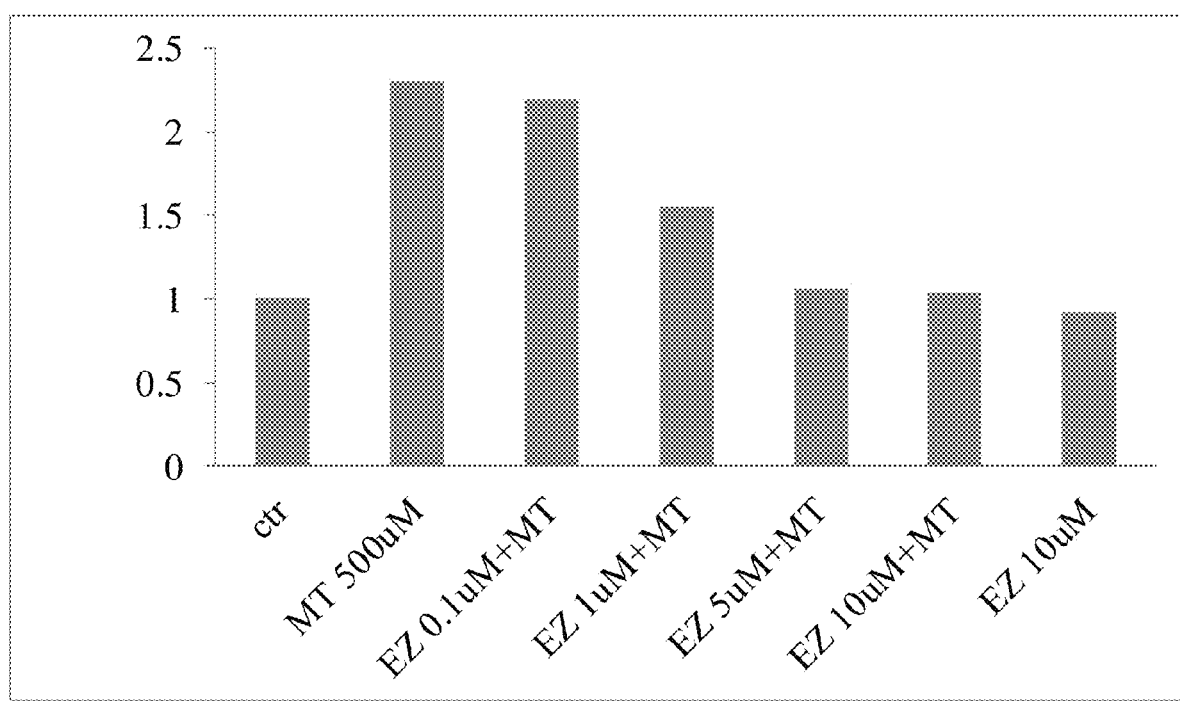
FIG. 9: Graph showing econazole effects on menthol (MT) induced ET1 mRNA expression in normal endothelial cells.

FIG. 9 shows the results where NL-MCECs were treated with menthol (MT, 500 µM), or MT (500 µM) after pretreatment with EZ (Econazole) solution for 30 minutes. The ET1 mRNA expression levels were detected by qPCR.

Overexpression of TRPM8 has functional consequences that contribute to MVEC dysfunction. Also, an increased expression of genes contributes to MVEC dysfunction by TRPM8 activation and near normalization of these genes by using TRPM8 antagonists, such as capsazepine. Stable formulations of TRPM8 antagonists are useful as topically applied antagonists as a therapeutic strategy for primary and secondary Raynaud's phenomenon.

Since capsazepine is not stable at room temperature and long term storage is recommended at −20° C., other TRPM8 antagonists were also evaluated for the purpose of treating Raynaud's phenomenon. Gel formulations of 3% econazole and 3% clotrimazole were prepared, then applied to the index and ring fingers (respectively) of the left hand of patients with Raynaud's phenomenon. The topical application was left for 15 minutes on the fingers, before inducing Raynaud's phenomenon by a cold challenge test. The digital blood flow was analyzed by infrared thermography.

The local application of econazole prevented the cold induced decrease in blood flow to the fingers after topical application, associated with a subjective feeling of less finger coldness by patient report. This provides clinical evidence for the role of the cold sensing receptor TRPM8 in Raynaud's phenomenon, and efficacy of blocking this axis as a modality to treat Raynaud's phenomenon.

This Example shows a favorable effect of using TRPM8 antagonists on SSc MVECs, and a favorable clinical effect by demonstrating that local application of TRPM8 antagonists is a useful strategy in the treatment of Raynaud's phenomenon. Human MVEC express functional TRPM8, and there is increased expression of TRPM8 in SSc skin and in SSc-MVEC. Without wishing to be bound by theory, it is now believed that TRPM8 is involved in cold-induced vascular dysfunction through increased ET1, and decreased NOS3 and PTGIS mRNA expression. The increased expression levels of TRPM8 in SSc-MVECs and SSc skin is now believed to mediate the known enhanced cold sensitivity in SSc. These results show that the blockade of TRPM8 activation can be an effective therapeutic strategy in SSc vasculopathy.

Example 2

An econazole compound was formulated with superior penetration through skin layers compared to commercially available econazole. This formulation ensures penetration of econazole through the skin to the dermal vasculature, where cold sensing receptors are expressed by microvascular endothelial cells. Interfering with TRPM8, a cold sensing receptor, will abolish cold induced vasospasm in Raynaud's phenomenon. Ensuring delivery of econazol (a TRPM8 antagonist) to the vasculature is important for achieving a topical therapy for Raynaud's phenomenon.

In this Example, described is the development of stable formulations of econazol nitrate 3%, such as a hydroxypropyl methylcellulose (HPMC) econazole nitrite dispersion formulation, that have excellent skin penetration.

Materials

Oleic Acid NF (Lot No. UV0230) was obtained from Spectrum Chemical (Gardena, Calif.). Butylated Hydroxyanisole (BHA) NF (Lot No. 2EC0250) was obtained from Spectrum Chemical (Gardena, Calif.). Ethylenediaminetetraacetic acid (EDTA), and disodium salt dehydrate, 99+% (Lot No. A0244379) were procured from ACROS (Fair Lawn, N.J.). Propylene Glycol USP/FCC (Lot No. 115135) was purchased from Fisher Scientific (Pittsburgh, Pa.). Ethanol 190 Proof (Lot No. 223512) was supplied by Decon Labs, Inc. (King of Prussia, Pa.). Hydroxypropyl methylcellulose (HPMC) (Methocel® E4M premium CR (hypromellose USP) (Lot No. C145201) was provided by PCCA (Houston, Tex.). Versabase® Cream (Lot No. 6654449) and PCCA Lipoderm Activemax were provided by PCCA (Houston, Tex.). Dimethyl sulphoxide (DMSO) HPLC grade (Lot No. 092056) was procured from Fisher Scientific (Pittsburgh, Pa.). Glycerin USP (Lot No. 2EG0467) was supplied by Spectrum Chemical (Gardena, Calif.). Econazole nitrate powder (Lot No. P11B013) was procured from Alfa Aesar (Ward Hill, Mass.). Sodium laureth sulphate (SLES), 100% pure (Lot No. 16134), was procured from Nature's Oil (Aurora, Ohio). Sodium chloride (Lot No. 075134) was provided by Fisher Scientific (Pittsburgh, Pa.). Polyethylene glycol 400, 100% (Lot No. 2603104) was supplied by Hampton research (Aliso viejo, CA). High Performance Liquid Chromatography (HPLC) solvents, including methanol (Lot No. 21063) and acetonitrile (Lot No. 18401), were purchased from Fisher Scientific (Pittsburgh, Pa.). Distilled deionized water was used throughout this Example.

Methods

Preparation of Formulations

Four topical formulations containing 3% econazole nitrate were prepared and characterized. The composition of the formulations is detailed in Table 1.

Econazole Nitrate Solution

A mixture of glycerin, propylene glycol, and oleic acid was prepared in a beaker and warmed up to 40° C. using a hot plate. Econazole nitrate was added to the mixture under continuous stirring. BHA and EDTA were added to the mixture. The volume of the mixture was made up to 100% using ethanol. The solution thus obtained was further characterized.

Econazole Nitrate HPMC Dispersion

Glycerin and propylene glycol mixture were added to HPMC polymer as a wetting agent and stirred using a magnetic stirrer. The required quantity of water was then added to the mixture to make a polymeric solution under stirring, and the mixture was left overnight for swelling of the polymer. Econazole nitrate was separately dissolved in a mixture of DMSO and ethanol, and vortexed thoroughly using a vortex mixer (VORTEX-T, Genie® 2). BHA and EDTA were added to the mixture. The drug solution was then added to the polymer solution and stirred carefully to avoid bubble formation.

Econazole Nitrate VersaBase® Cream

Econazole nitrate was dissolved in DMSO and the mixture was vortexed thoroughly using a vortex mixer (VORTEX-T, Genie® 2). BHA and EDTA were added to the mixture. The weight was made up to 100% with Versabase® cream base. The cream was then homogenized with a hand homogenizer.

Econazole Nitrate Lipoderm® Activemax™ Cream

Econazole nitrate was dissolved in DMSO and the mixture was vortexed thoroughly using a vortex mixer (VORTEX-T, Genie® 2). BHA and EDTA were added to the mixture. The weight was made up to 100% with Lipoderm® Activemax™ cream base. The cream was then homogenized with a handheld homogenizer.

TABLE 1

Composition of 3% econazole nitrate formulations

| Ingredients | Topical solution (F1) (% w/w) | HPMC dispersion (F2) (% w/w) | VersaBase® cream (F3) (% w/w) | Lipoderm® Activemax™ Cream (F4) (% w/w) |
|---|---|---|---|---|
| Econazole nitrate | 3 | 3 | 3 | 3 |
| Propylene glycol | 50 | 10 | — | — |
| Glycerin | 10 | 10 | — | — |
| Oleic acid | 10 | — | — | — |
| DMSO | — | 40 | 30 | 30 |
| Hydroxypropyl methylcellulose | — | 1 | — | — |
| Butylated Hydroxyanisole | 0.05 | 0.05 | 0.05 | 0.05 |
| Ethylenediamine-tetraacetic acid | 0.10 | 0.10 | 0.10 | 0.10 |
| VersaBase® cream** | — | — | q.s. to 100 | — |
| Lipoderm® Activemax™ Cream** | — | — | — | q.s. to 100 |
| Ethanol | q.s. to 100 | 10 | — | — |
| Water | — | q.s. to 100 | — | — |

**Topical cream base developed by PCCA

HPLC Chromatographic Conditions of Econazole Nitrate

Figure 10:
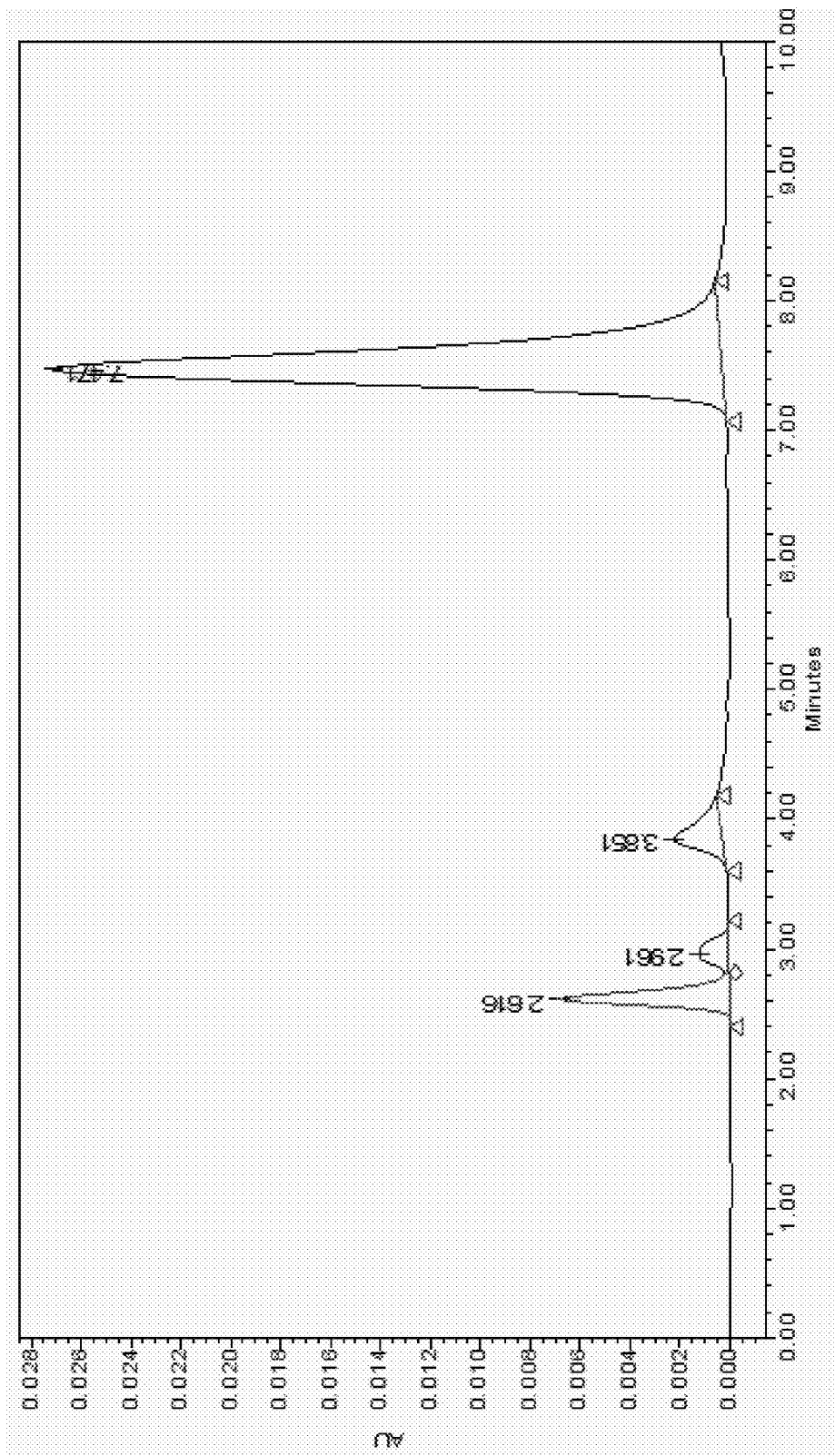
FIG. 10: HPLC chromatogram of econazole nitrate.
Figure 11:
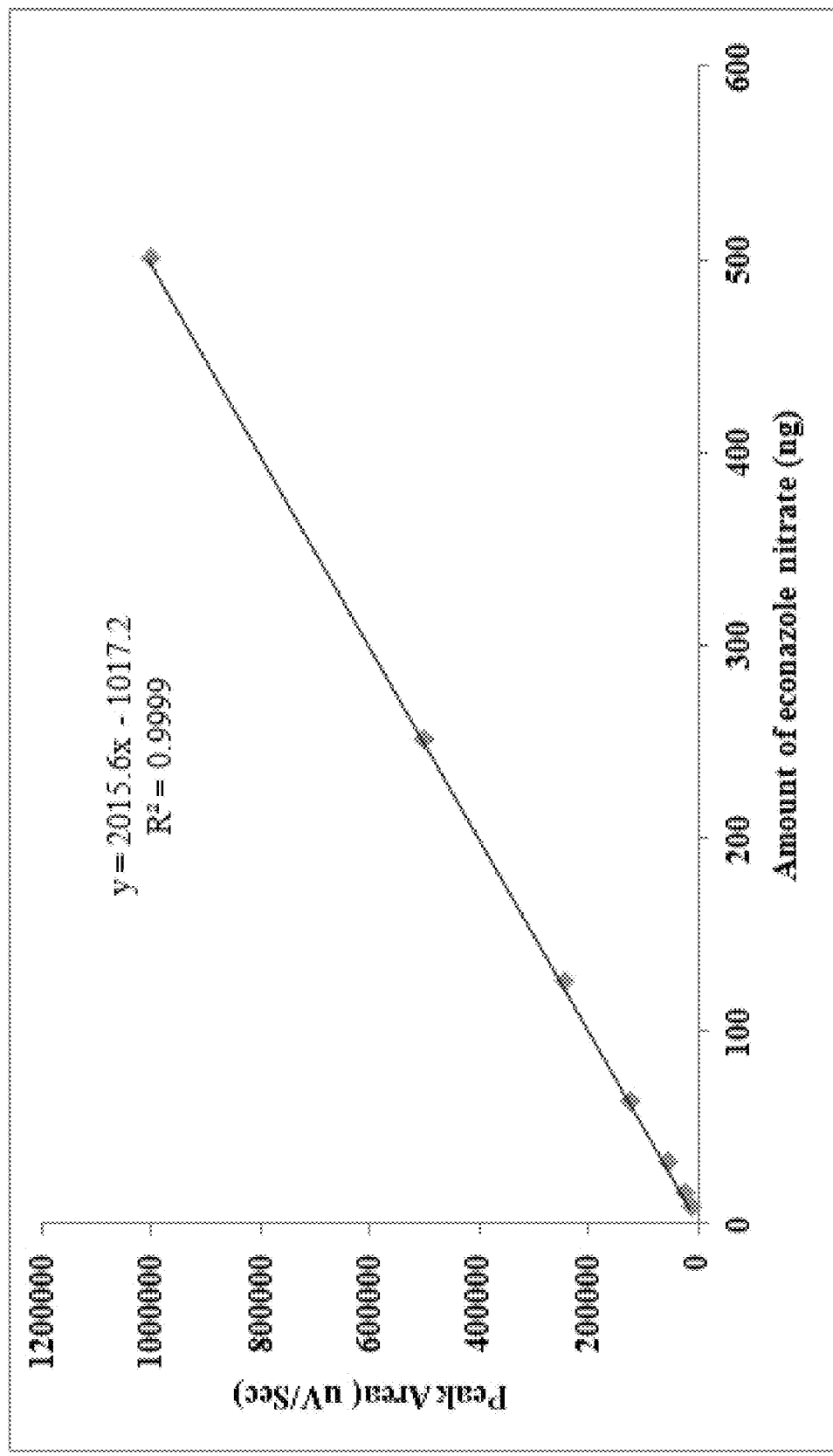
FIG. 11: Calibration curve of econazole nitrate in the mobile phase.

A high-performance liquid chromatography (HPLC) method was developed and validated for drug content determination. A HPLC (Waters Alliance e2695 separation module, Milford, Mass.), equipped with a 2998 PDA detector and reverse-phase C18 column (Dimension mm: 250×4.6 mm) (5 µm, Hypersil™ ODS, Thermos scientific, MA), was used to analyze econazole nitrate in the formulations. An isocratic method was used for analysis with a mobile phase containing methanol/0.05 M ammonium dihydrogen phosphate (ADP), pH 3.4 (85:15), pumped at a flow rate of 1 ml/min. The retention time of econazole nitrate ($\lambda_{max}$=230 nm) was found to be 7.471 minutes (FIG. 10). A stock solution (1 mg/ml) of econazole nitrate was prepared in the mobile phase and calibration standards ranging from (0.195-50 µg/ml) were serially diluted in the mobile phase. Each standard was analyzed in triplicate. A calibration curve was made by plotting the average peak area against the amount of drug. A straight line (y=2015.6x−1017.2) was obtained with a correlation coefficient ($r^2$) value of 0.9999 (FIG. 11). The percentage recovery of econazole nitrate ranged from 98.19% to 103.34% (between 95%-105%). The inter day precisions of econazole nitrate were satisfactory—0.4711% (RSD<2%). The limit of detection (LOD) of econazole nitrate was found to be 0.296 μg/ml and limit of quantification (LOQ) was found to be 0.895 μg/ml.

Figure 12:
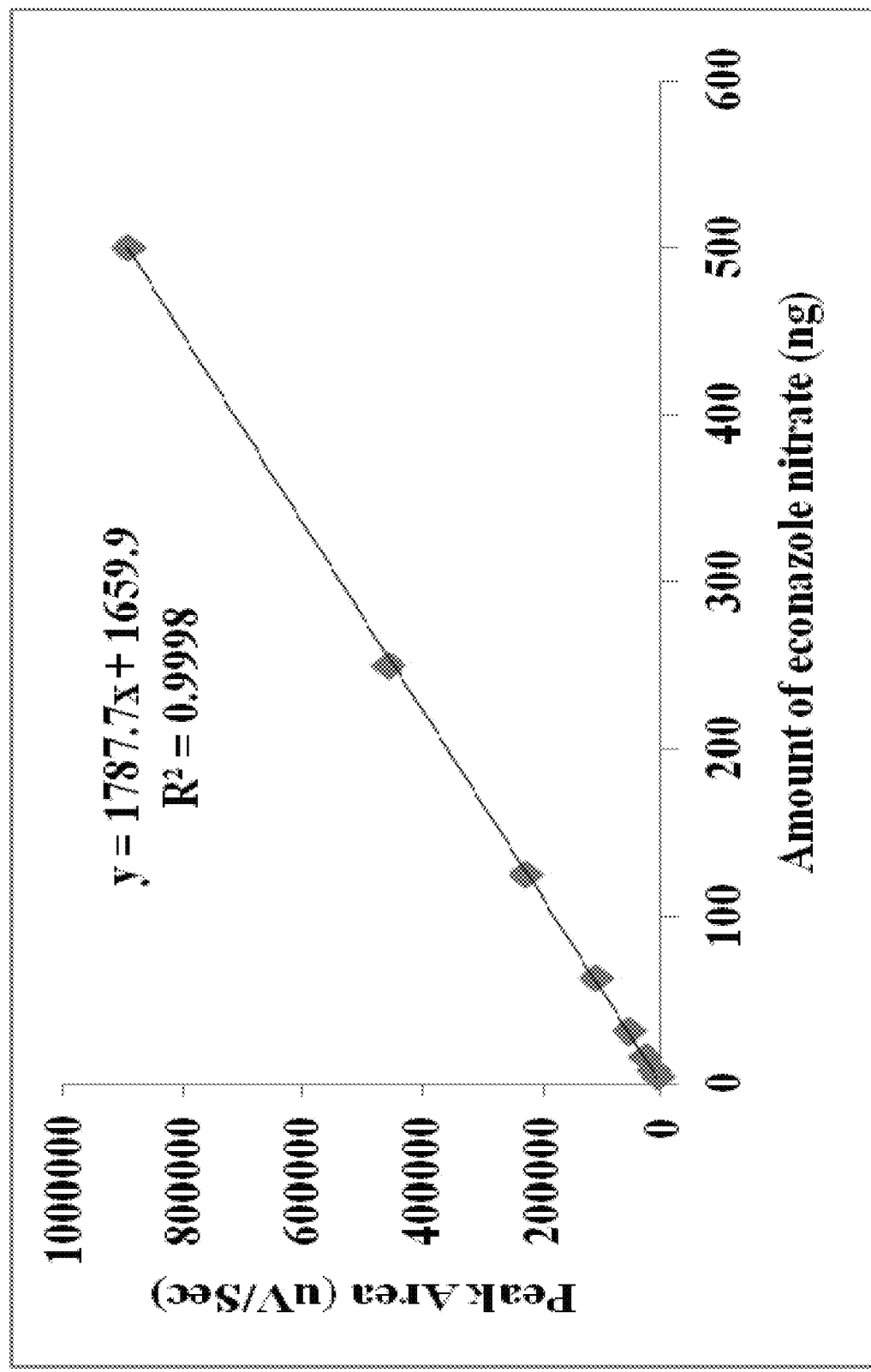
FIG. 12: Calibration curve of econazole nitrate in DMSO.

Another standard curve was prepared similarly in DMSO. A straight line (y=1787.7x−1659.9) was obtained with a correlation coefficient ($r^2$) value of 0.9998 (FIG. 12).

The drug content of formulation F1 was determined by making a suitable dilution in the mobile phase. The drug content of formulations F2, F3, and F4 was determined by making sample dilutions in DMSO. The drug content of all formulations was determined in triplicate.

Determination of pH

For determination of pH of formulations F1 and F2, the electrode was directly dipped into formulations and the pH was noted. For formulations F3 and F4, 0.2 g of the cream was dispersed and stirred for 2 h in 20 ml of distilled deionized water, and the pH was determined using a Mettler Toledo pH meter (Mettler-Toledo Ingold Inc., Billerica, Mass. USA). The pH meter was calibrated with standard buffer solutions of pH 4, 7, 10 before each use.

Stability Study

Stability tests were performed to examine the physical and chemical stability of the formulations. Samples of F1 and F2 were placed in Eppendorf tubes and stored at 25° C. and 35° C./70% RH. Samples of F3 and F4 formulations were stored at 4° C. and 25° C. At regular time intervals of 0, and 15 days, and 1, 2, and 3 months, the formulations were analyzed for pH and drug content. The stability study was performed in triplicate.

Differential Scanning Calorimetry (DSC)

DSC analysis was carried out for the pure drug, blank formulations, and drug loaded formulations (F1, F2, F3, and F4) to examine the physical state, thermal properties, and the rate of heat absorbed by econazole nitrate after loading into the formulations. Samples were characterized using a Differential Scanning calorimeter (DSC) (822e Mettler Toledo, GmbH, Schwerzenbach, CH) equipped with a TS0800GCI gas flow system attached to a nitrogen gas cylinder and the TSO801RO sample robot. All samples (5-10 mg) were sealed and placed in 100 μl aluminum crucibles using the Mettler MT 5 microbalance. DSC studies were done at a 10° C./min heating rate over a wide range (25-250° C.). Stare SW 10.00 was used to take the scans. Nitrogen gas was purged at a rate of 10 ml/min.

Percutaneous Absorption of Econazole Nitrate Across Porcine Ear Skin

The formulation permeation study across porcine ears was carried out for the prepared formulations and compared with marketed econazole nitrate (1%) cream. Porcine ears were obtained from a nearby slaughterhouse (Kastel's Slaughter House & Processing Center, Riga, Mich.). During the transport and cleaning procedures the tissues were placed in an ice cold PBS buffer (pH 7.4) solution. The dorsal ear skin was separated from the ear cartilage. The hair on the skin samples was removed gently with a razor. After hair removal, subcutaneous fat was carefully removed with a scalpel. The thickness of the skin was measured at five different places with a digital electronic micrometer (Mitutoyo Corporation, Japan), and average thickness was recorded. Tissues were stored at −20° C. by applying glycerin on both sides and wrapping them in aluminum foil with no folds. All tissues were used in less than 2 months.

Figure 13:
FIG. 13: Photograph of a PermeGear static glass cell.

Around 2 cm$^2$ skin specimens were cut and mounted between the receptor and donor chambers of Franz diffusion cells (PermeGear Inc., Hellertown, Pa.) (FIG. 13). The cells were placed on a magnetic stirrer and the water jacket temperature was maintained at 34.2±1° C. with a circulating water bath. The receptor chamber was filled with saline containing 30% PEG 400. The tissues were equilibrated for one hour before initiating the study till their temperature reached 32° C. The outer surface of the skin was placed towards the donor chamber. The permeability study was initiated by placing 500 mg of marketed formulation or an equivalent amount of drug loaded formulations in the donor chamber. An aliquot (500 μl) was withdrawn at 30 min, 1, 2, 4, 6, 8, 12, and 16 h and replaced with an equal amount of fresh receptor fluid. Care was taken to prevent the air bubble formation in between skin and receptor fluid during the entire duration of the study.

After 16 hours, the donor chamber formulation was washed with the help of q-tips and 5% SLES (3 times, 2 ml each time), and stored in glass vials. The skin samples were removed from the Franz cells and separated into the stratum corneum, epidermis, and dermis. The drug was extracted from the skin layers and analyzed using the above-described HPLC method. The drug concentration in the washing solution and the receptor fluid was also analyzed for mass balance recovery. Any cells outside the mass balance recovery range of 100±20% econazole nitrate were excluded. The average of each of these values for formulation F1, F2, F3, and F4 were compared with averages of marketing formulation.

Results and Discussion

Four different formulations containing 3% econazole nitrate were successfully prepared with desired physical and visual characteristics. Formulation F1 was a clear topical solution with slightly higher viscosity. Formulation F2 was an HPMC dispersion that exhibited a loosely structured translucent gel consistency. Formulations F3 and F4 were both off white and showed cream consistency. All formulations were evaluated for drug content, pH, stability, DSC, FTIR, pXRD, and in vitro permeation. The drug content of all four formulations was found to be in the desired limits of 95%-105% (Table 2). This indicates the uniform distribution of the drug in the formulations. The pH of all formulations was found to be in between 4-5, which is in the desired range of topical formulations applied to the skin. Variable skin pH values ranging from pH 4.0 to 7.0 are reported in literature. It is believed that the formulations will not cause any pH-induced irritation.

TABLE 2

Drug content and pH measurements of formulations. Values expressed as mean ± standard deviation; F1-Econazole Nitrate Solution (3%); F2-Econazole Nitrate HPMC Dispersion (3%); F3-Econazole Nitrate Versabase ® cream (3%); F4-Econazole Nitrate Lipoderm ® Activemax ™ Cream (3%).

| Formulation | Drug content | pH |
| --- | --- | --- |
| F1 | 102.83 ± 0.53 | 4.212 ± 0.0257 |
| F2 | 100.15 ± 0.37 | 4.475 ± 0.0250 |
| F3 | 100.02 ± 0.78 | 5.060 ± 0.183 |
| F4 | 104.14 ± 0.14 | 4.557 ± 0.031 |

The formulations were stored at different temperatures and relative humidity conditions and were evaluated for stability. The drug content and pH values are shown in Table 2. All four formulations were found to be physically and chemically stable at the reported storage conditions up to 3 months. The drug content values were found to be in the range of 95.93%-105.90% and no significant changes in pH were observed (Table 3). Formulations F1 and F2 at 4° C. were eliminated, as both displayed crystal growth on refrigeration.

(F3 and F4) showed broad endotherms close to the melting of econazole nitrate. This could be due the presence of undissolved/crystalline drug in the cream formulations.

TABLE 3

Drug content and pH values of stability samples. Values expressed as mean ± standard deviation; F1-Econazole Nitrate Solution (3%); F2-Econazole Nitrate HPMC Dispersion (3%); F3-Econazole Nitrate Versabase cream (3%); F4-Econazole Nitrate Lipoderm Activemax Cream (3%).

| Storage condition | F1 | F2 | F3 | F4 |
|---|---|---|---|---|
| 4° C. | | | | |
| Drug content | Not performed | Not performed | 102.98 ± 4.71 | 103.33 ± 1.53 |
| pH | Not performed | Not performed | 5.123 ± 0.035 | 4.564 ± 0.0187 |
| 25° C. | | | | |
| Drug content | 96.35 ± 1.78 | 105.90 ± 4.15 | 99.01 ± 0.73 | 101.34 ± 1.43 |
| pH | 4.418 ± 0.026 | 4.592 ± 0.019 | 5.023 ± 0.014 | 4.554 ± 0.013 |
| 35° C./70% RH | | | | |
| Drug content | 95.93 ± 5.3 | 102.17 ± 1.44 | Not performed | Not performed |
| pH | 4.318 ± 0.007 | 4.598 ± 0.013 | Not performed | Not performed |

Figure 14A:
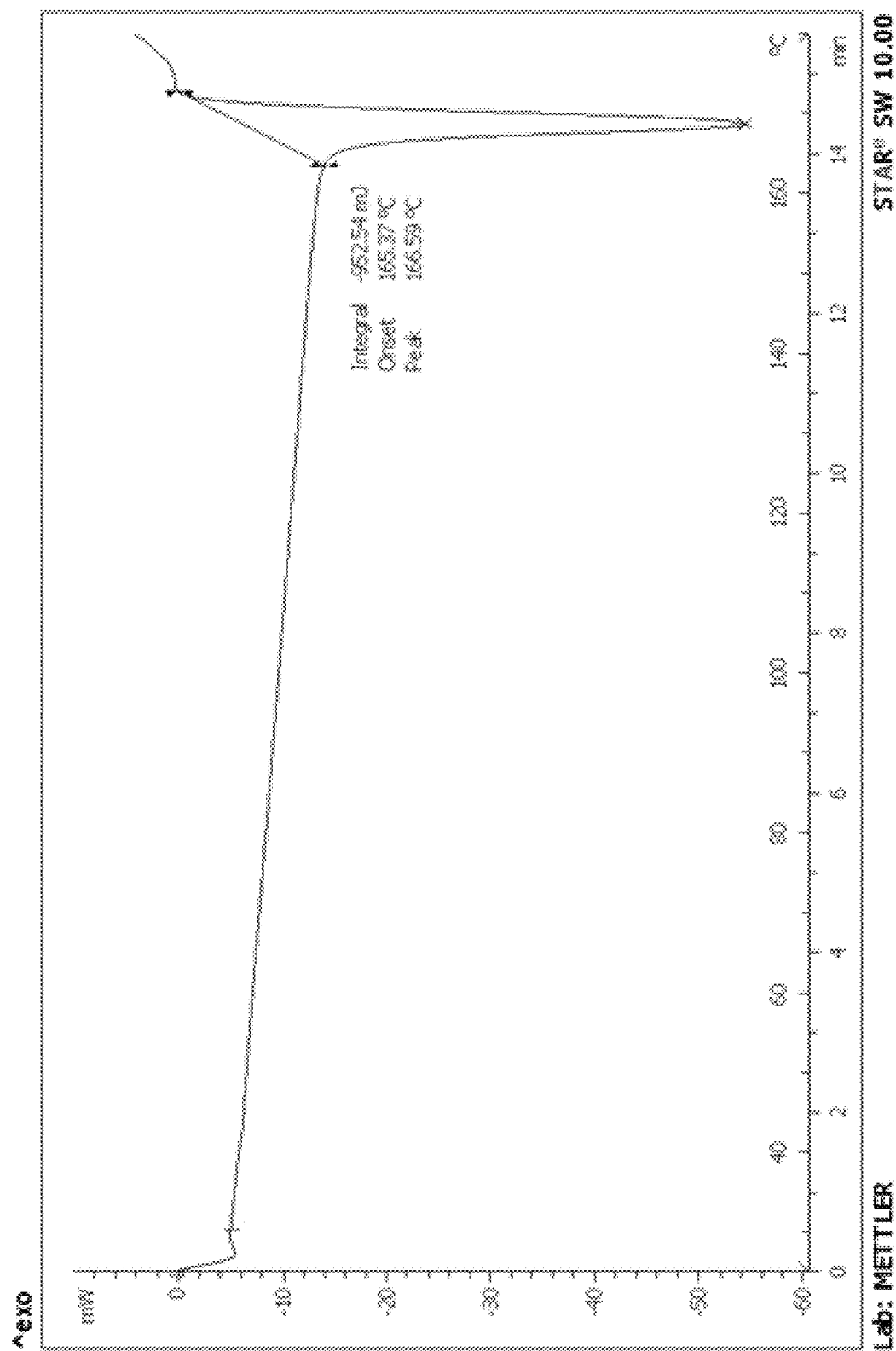
FIGS. 14A-14E: DSC thermogram of econazole nitrate (FIG. 14A), formulation F1 (red) and its corresponding blank (black) (FIG. 14B), formulation F2 (black) and its corresponding blank (red) (FIG. 14C), formulation F3 (black) and its corresponding blank (red) (FIG. 14D), and formulation F4 (red) and its corresponding blank (black) (FIG. 14E). F1—Econazole Nitrate Solution (3%); F2—Econazole Nitrate HPMC Dispersion (3%); F3—Econazole Nitrate Versabase® cream (3%); F4—Econazole Nitrate Lipoderm® Activemax™ Cream (3%).
Figure 14B:
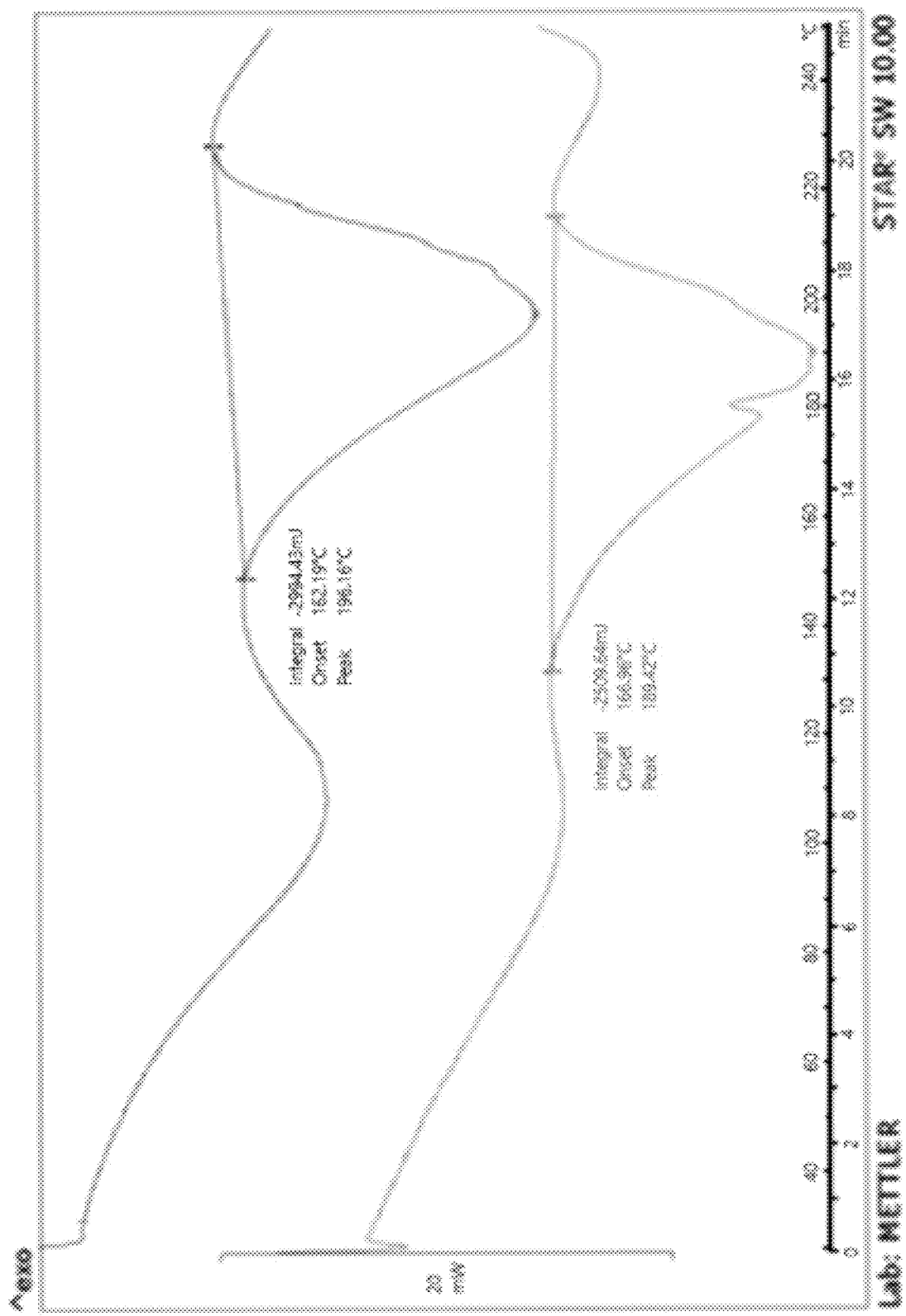
Figure 14C:
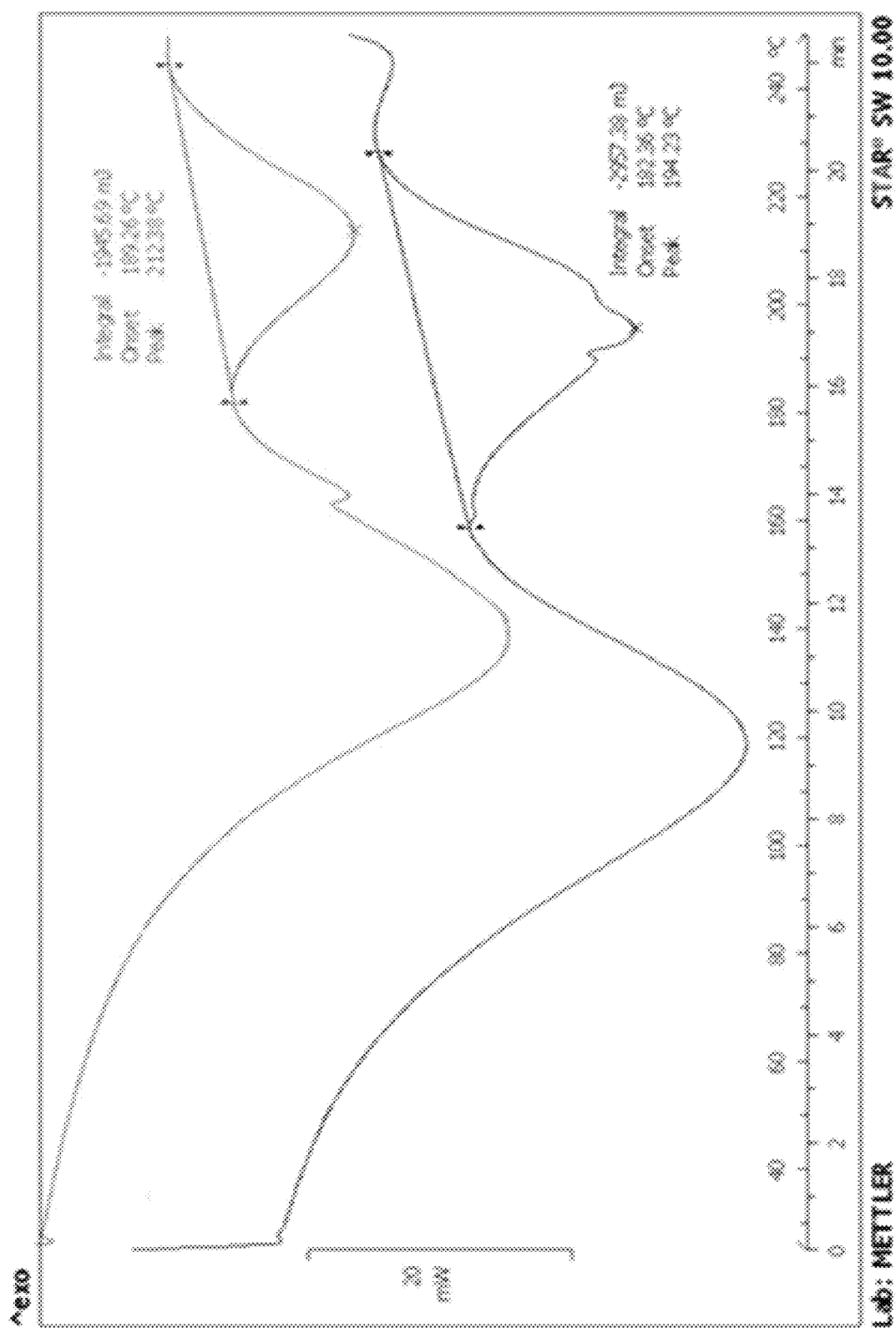
Figure 14D:
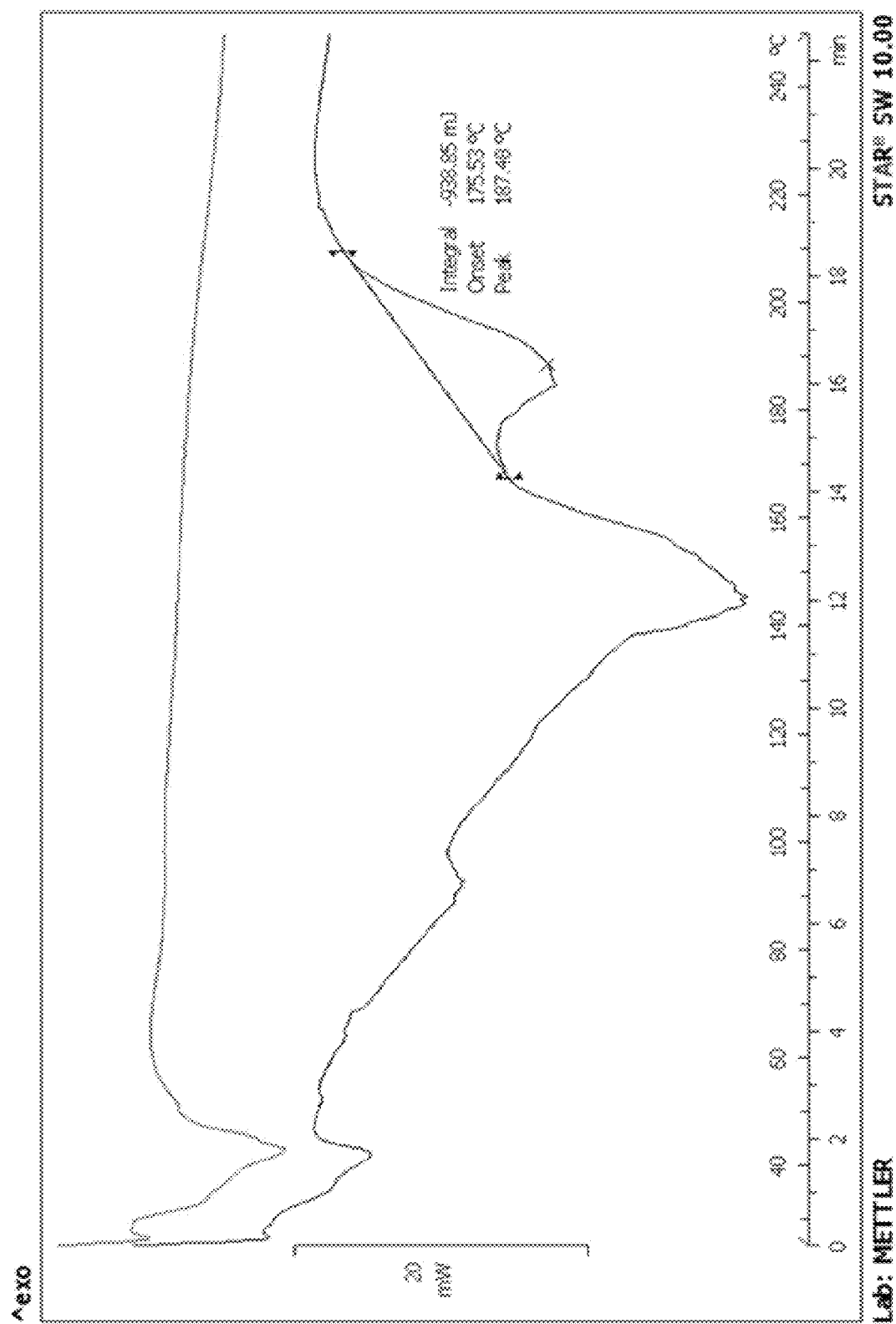
Figure 14E:
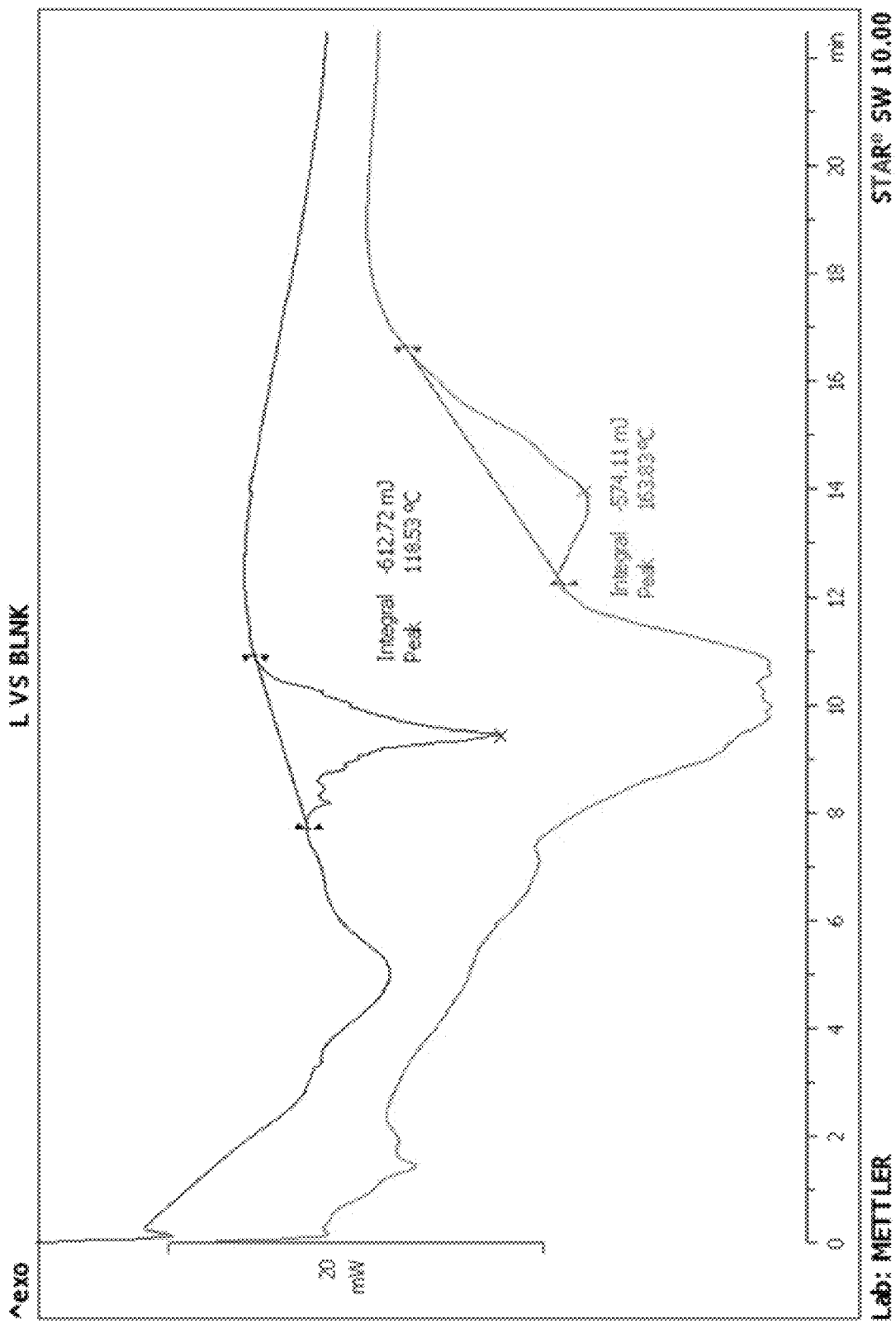

A DSC study was carried out to verify the absence of any un-dissolved drug in the formulations. DSC thermograms of the pure drug, F1, F2, F3, and F4 formulations, and their corresponding blanks, are shown in FIGS. 14A-14E. The pure drug exhibited a sharp endothermic peak at around 165° C. (FIG. 14A), which corresponds to its theoretical melting point of 162° C. Blank formulation F1 showed a wide endothermic peak at 196° C., which could be due to its components, whereas the drug loaded formulation exhibited a slightly shifted endotherm at 189° C., and a small endothermic bump at about 180° C., neither of which corresponds to the melting point of drug (FIG. 14B). Two significantly broad endotherms at 140° C. and 212° C. were observed in the blank formulation F2, both of which are slightly shifted to 120° C. and 194° C. in the drug loaded formulation (FIG. 14C). Blank formulation F3 showed a broad endothermic peak at 40° C., while the corresponding drug loaded formulation showed an additional wide endothermic peak at about 145° C. and 175° C. (FIG. 14D). Similarly, the blank formulation F4 exhibited an endotherm at 118° C., and the drug loaded F4 exhibited endotherms at 120° C. and 163° C. (FIG. 14E). Both cream formulations Percutaneous absorption of econazole nitrate from the formulations was carried out across pig ear skin and compared with the marketed formulation. Pig ear skin was used as it is believed to have permeability characteristics similar to human skin. The amount of econazole nitrate penetrated through various skin layers such as stratum corneum, epidermis, and dermis, is shown in Table 4. The amount of drug permeated through the skin and remaining in the donor chamber was also analyzed to calculate the mass balance (Table 4). Overall mass balance was within the acceptable range of 100±20%.

TABLE 4

Percutaneous absorption of econazole nitrate across porcine ear skin. Values expressed as mean ± standard deviation; F1-Econazole Nitrate Solution (3%); F2-Econazole Nitrate HPMC Dispersion (3%); F3-Econazole Nitrate Versabase cream (3%); F4-Econazole Nitrate Lipoderm Activemax Cream (3%).

| | Percent drug penetrated into skin layers | | | Percent drug permeated | Percent drug remaining in the |
|---|---|---|---|---|---|
| Formulation | Stratum corneum | Epidermis | Dermis | through the skin | donor chamber |
| F1 | 2.14 ± 1.36 | 1.01 ± 0.53 | 1.74 ± 0.38 | 2.28 ± 0.40 | 85.35 ± 2.36 |
| F2 | 2.73 ± 0.67 | 2.18 ± 0.99 | 3.29 ± 1.17 | 10.27 ± 0.76 | 82.45 ± 5.14 |
| F3 | 1.02 ± 0.29 | 0.75 ± 0.30 | 1.51 ± 0.50 | 1.47 ± 0.30 | 96.14 ± 1.05 |
| F4 | 2.64 ± 0.33 | 1.21 ± 0.67 | 1.88 ± 0.39 | 2.47 ± 0.73 | 93.77 ± 2.75 |
| Marketed formulation | 0.24 ± 0.04 | 0.09 ± 0.04 | 0.19 ± 0.04 | 0.22 ± 0.08 | 82.67 ± 2.90 |

Based on the percutaneous absorption data shown in Table 4, the order of amount of drug permeated from highest to lowest was F2 (10.27%±0.76%)>F4 (2.47±0.73)>F1 (2.28%±0.40%)>F3 (1.47%±0.30%)>marketed formulation (0.22%±0.08%). Econazole nitrate HMPC dispersion showed the highest permeation, which was almost 50-fold higher than the marketed formulation and approximately 5-fold higher than other formulations. Similarly, a higher concentration of econazole nitrate was observed in the stratum corneum, epidermis, and dermis with F2. Greater permeation of econazole nitrate from HPMC dispersion may be due to the presence of DMSO in higher concentration compared to other formulations. DMSO is a penetration enhancer for topical and transdermal formulations. The mechanism of the chemical increasing the permeation lies in fluidization and interaction of the stratum corneum lipids with DMSO and facilitating transport. All four formulations exhibited better penetration and permeation of econazole nitrate across the pig ear skin compared to the marketed formulation. In sum, this Example shows that formulation F2 is useful as a treatment option for Raynaud's phenomenon.

Certain embodiments of the present disclosure are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

What is claimed is:

1. A topical formulation comprising:
   a transient receptor potential melastatin-8 (TRPM-8) antagonist composition in an amount sufficient to block TRPM8 signaling pathways in skin cells, wherein the TRPM-8 antagonist comprises econazole or a salt thereof at a concentration of 3% w/w;
   hydroxypropyl methylcellulose present at a concentration of 1% w/w;
   dimethyl sulfoxide (DMSO) present at a concentration of 40% w/w; and
   ethanol in an amount of 10% w/w;
   wherein the topical formulation has a pH in a range of from 4 to 5.

2. The topical formulation of claim 1, wherein the TRPM-8 antagonist comprises econazole nitrate.

3. The topical formulation of claim 1, further comprising one or more of propylene glycol, glycerin, butylated hydroxyanisole, ethylenediaminetetraacetic acid (EDTA), and water.

4. The topical formulation of claim 1, wherein the transient receptor potential melastatin-8 (TRPM-8) antagonist comprises a gel formulation of econazole.

5. The topical formulation of claim 1, wherein the formulation is in the form of a topical gel, lotion, foam, cream, spray, aerosol, ointment, suspension, emulsion, microemulsion, nanoemulsion, liposomal system, niosomes, solid lipid nanoparticles, lacquer, patch, or bandage.

6. The topical formulation of claim 5, wherein the topical gel delivers an effective amount of the TRPM-8 antagonist to a region of intact skin sufficient to improve vascular spasm.

7. The topical formulation of claim 1, further containing at least one cosmetically acceptable humectant, emollient, or softening agent.

8. A method for inhibiting transient receptor potential melastatin-8 (TRPM-8) in skin cells, comprising: topically administering an effective amount of the topical formulation of claim 1.

9. A method of treating Raynaud's phenomenon comprising the steps of:
   identifying a subject suffering from Raynaud's phenomenon, and
   topically administering to the subject a pharmaceutical composition comprising the topical formulation of claim 1, in an amount effective to treat Raynaud's phenomenon.

10. A topical formulation comprising:
    a transient receptor potential melastatin-8 (TRPM-8) antagonist composition in an amount sufficient to block TRPM8 signaling pathways in skin cells, wherein the TRPM-8 antagonist comprises econazole or a salt thereof at a concentration of 3% w/w;
    propylene glycol present at a concentration of 10% w/w;
    glycerin present at a concentration of 10% w/w;
    hydroxypropyl methylcellulose present at a concentration of 1% w/w;
    dimethyl sulfoxide (DMSO) present at a concentration of 40% w/w;
    butylated hydroxyanisole present at a concentration of 0.05% w/w;
    ethylenediaminetetraacetic acid present at a concentration of 0.10% w/w;
    ethanol present at a concentration of 10% w/w; and
    water;
    wherein the topical formulation has a pH of 4.475±0.0250.

* * * * *